United States Patent [19]
Okarma et al.

[11] Patent Number: 5,730,713
[45] Date of Patent: *Mar. 24, 1998

[54] REMOVAL OF SELECTED FACTORS FROM WHOLE BLOOD OR ITS COMPONENTS

[75] Inventors: Thomas B. Okarma, Palo Alto; John Blankenship, Santa Clara; Abraham T. Lin, Palo Alto; Mohammad A. Elkalay, Cupertino, all of Calif.

[73] Assignee: Rhone-Poulenc Rorer Pharmaceuticals Inc., Collegeville, Pa

[*] Notice: The term of this patent shall not extend beyond the expiration date of Pat. No. 5,523,096.

[21] Appl. No.: 657,239

[22] Filed: Jun. 3, 1996

Related U.S. Application Data

[63] Continuation of Ser. No. 482,315, Jun. 6, 1995, Pat. No. 5,523,096, which is a continuation-in-part of Ser. No. 32,357, Mar. 16, 1993, Pat. No. 5,437,861.

[51] Int. Cl.$^6$ .......................... A61K 35/14; A61M 1/14; A61M 37/00
[52] U.S. Cl. .................. 604/6; 604/5; 424/489; 422/44
[58] Field of Search .................. 422/44; 604/5, 604/6

[56] References Cited

U.S. PATENT DOCUMENTS

| | | |
|---|---|---|
| 3,522,346 | 7/1970 | Chang ............................. 422/44 |
| 3,607,857 | 9/1971 | Nelson . |
| 3,998,946 | 12/1976 | Condie et al. . |
| 4,006,059 | 2/1977 | Butler . |
| 4,059,685 | 11/1977 | Johnson . |
| 4,072,566 | 2/1978 | Lynn . |
| 4,102,746 | 7/1978 | Goldberg . |

(List continued on next page.)

FOREIGN PATENT DOCUMENTS

| | | | |
|---|---|---|---|
| 0219053 | 4/1987 | European Pat. Off. ............. 422/44 |
| 3109123 | 9/1982 | Germany . |
| 61-58664 | of 0000 | Japan . |
| 61-58664 | 3/1986 | Japan ............................. 422/44 |
| 1 536 425 | 12/1978 | United Kingdom . |
| WO 88/09202 | 12/1988 | WIPO . |
| WO 90/00903 | 2/1990 | WIPO . |

OTHER PUBLICATIONS

Lee et al., Hemofiltration Removes Toxic Mediators and Prolongs Survival in Staphylococcus Aureus Sepsis Acute Lung Injury, Am. Rev. Respir. Dis. 141:A140 (1990).

Matson et al., Continuous Arteriovenous Hemofiltration (CAVH) therapy for Sepsis–Induced Acute Lung Injury in Immature Swine, FASEB J. 4(4):A953 (1990).

(List continued on next page.)

*Primary Examiner*—P. F. Kulkosky

[57] ABSTRACT

This invention provides a composition, device and method for the removal of selected factors, such as cytokines or pharmaceuticals, from a substance such as whole blood or plasma. Advantageously, the invention provides for the treatment or prevention of septic shock syndrome or other conditions evidenced by the presence of cytokines in a patient by contacting the patient's whole blood with a composition comprising silica and a surface treatment material, such as heparin, but preferably human serum albumin (HSA). The treatment lowers the cytokine concentration of the blood. Pharmaceuticals can be removed from an individual's whole blood or plasma, such as for use in treating drug overdosage.

42 Claims, 23 Drawing Sheets

U.S. PATENT DOCUMENTS

| | | |
|---|---|---|
| 4,420,395 | 12/1983 | Tanihara et al. . |
| 4,472,303 | 9/1984 | Tanihara et al. . |
| 4,728,432 | 3/1988 | Sugiyama et al. . |
| 4,748,121 | 5/1988 | Beaver et al. . |
| 4,787,974 | 11/1988 | Ambrus et al. . |
| 4,861,707 | 8/1989 | Balint, Jr. et al. . |
| 4,865,841 | 9/1989 | Balint, Jr. . |
| 4,883,765 | 11/1989 | Tamir et al. . |
| 4,963,265 | 10/1990 | Okarma et al. . |
| 5,022,988 | 6/1991 | Okarma et al. . |
| 5,041,079 | 8/1991 | Takashima et al. . |
| 5,294,401 | 3/1994 | Hagiwara . |
| 5,421,815 | 6/1995 | Noguchi et al. . |
| 5,437,861 | 8/1995 | Okarma et al. . |
| 5,523,096 | 6/1996 | Okarma et al. ............................ 422/44 |

OTHER PUBLICATIONS

Molines et al., Formation of C5a During Cardiopulmonary Bypas: Inhibition by Precoating With Heparin, Ann. Throrac. Surg. (1991) 52:92–97.

Tamiya et al., Significance of the concentrated red cell and albumin priming method with particular reference to anaphylatoxin generation, J. Thorcic & Cardiovascular Surg. (1992) 103(1):78–86.

Murugavel, In Vitro Studies of the Efficacy of Reversed Phase Silica Gel as a Sorbent for Hemo– and Plasmaperfusion, J. Toxicol (1992) 30(1):69–82.

Bol'shakov et al., Protective Effect of Anti–staphylococcal Immunosorbent on the Phenotype of Lymphocyte Membrane in Diffuse Staphylococcus–Pseudomonas Peritonitis, Vestn. Akad. Med. Nauk. SSSR 7:36–40. (1991).

Lin et al., Laboratory Evaluation of Hemoperfusion Adsorptive Resin Column for the Treatment of Sepsis and Septic Shock, Abst. American Society for Aphersis, 13th Annual Mtg. (1992).

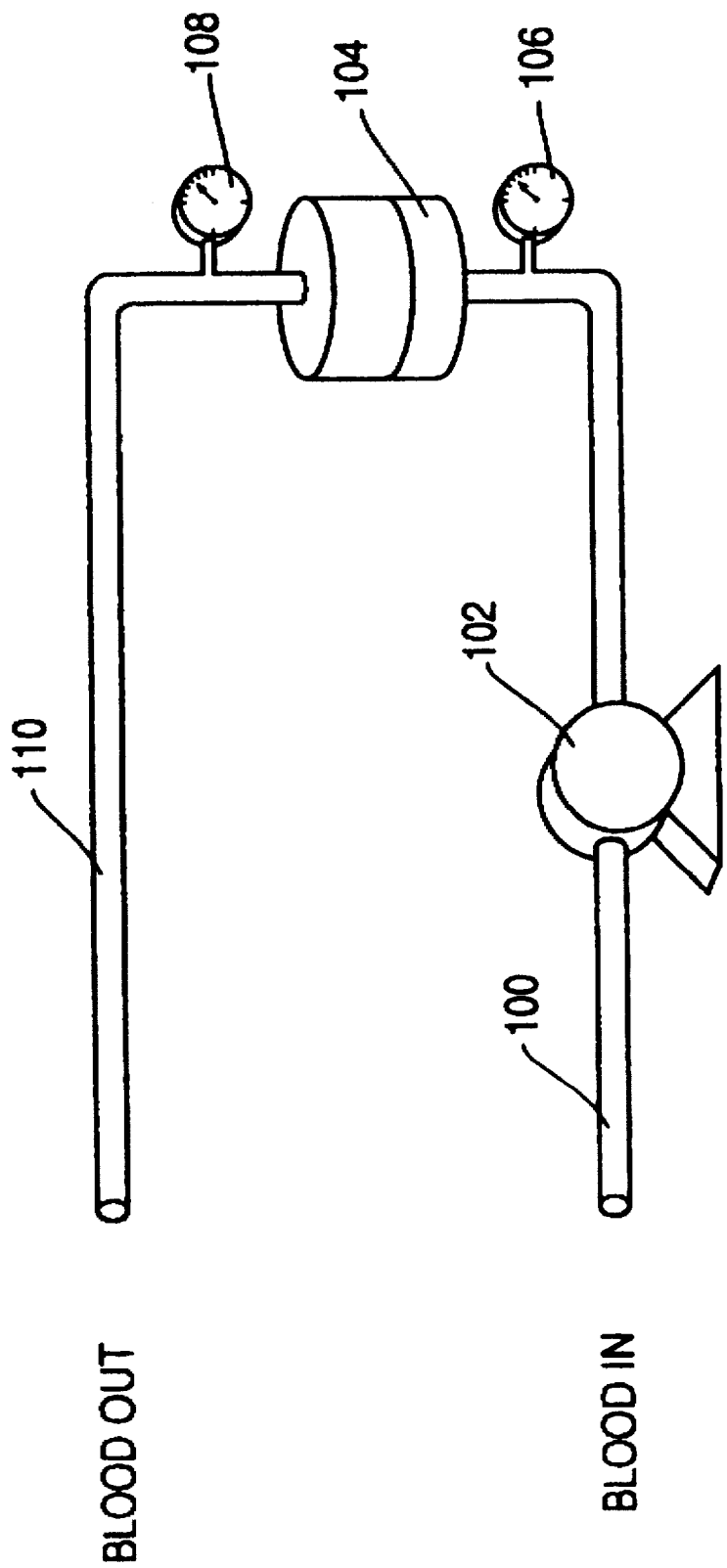

REMOVAL OF SELECTED FACTORS FROM WHOLE BLOOD OR ITS COMPONENTS

CROSS REFERENCE TO RELATED APPLICATIONS

This is a continuation of application Ser. No. 08/482,315 filed on Jun. 6, 1995, now U.S. Pat. No. 5,523,096 which is a continuation-in-part of U.S. patent application Ser. No. 08/032,357 filed on Mar. 16, 1993, now U.S. Pat. No. 5,437,861.

FIELD OF THE INVENTION

This invention concerns the treatment and prevention of conditions evidenced by the presence of selected factors in a patient's blood. More specifically, the invention concerns the treatment and prevention of septic shock syndrome and capillary leak syndrome, diseases which correlate with the presence of selected factors such as cytokines, serotonin, histamine, and/or activated complement components in a patient's blood. Alternatively, the invention is used to remove selected factors such as pharmaceuticals from a patient's blood. In a preferred form, the method of the invention is performed by extracorporeally contacting the patient's whole blood with a composition comprising silica and a surface treatment material, such as heparin, but preferably human serum albumin (HSA). Thereby, the selected factor concentration in the blood is lowered. Furthermore, the method may also be used to remove selected factors from blood components.

BACKGROUND OF THE INVENTION

Septic shock is a serious syndrome which most often accompanies gram-negative, and sometimes gram-positive, bacteremia. However, septic shock may occur in virtually any typical infection, e.g., viral, fungal, and rickettsial; it may also result from severe trauma or tissue injury. For example, gram-negative rods such as Enterobacteriaceae and Pseudomonaceae are normally found in the digestive tract, however, these bacteria can invade the bloodstream of patients receiving immunosuppressive therapy; or patients who have experienced trauma, burns, major surgical procedures, or organ transplantations, or diseases such as cystic fibrosis, renal insufficiency and malignant neoplasms. Once the bacteria have invaded the bloodstream, they become capable of inducing septic shock.

Septic shock usually results from a series of events triggered by bacteremia during which bacterial cell wall substances (endotoxin in gram-negative organisms and peptidoglycan/teichoic acid complex in gram-positive organisms) cause excessive activation of the cytokine, complement, coagulation factor, kinin, and ACTH/endorphin systems. Eventually, overactivation of these various systems results in a series of self-induced cardiovascular and metabolic events that progress to a state of circulatory collapse, shock and organ dysfunction.

Incipient septic shock is characterized by body temperature extremes (hypothermia or fever), orthostatic blood pressure decrease, decreasing urine output, edema, falling serum albumin concentration, development of a metabolic acidosis, elevated serum lactate, thrombocytopenia, and the like. Overall, the current concept of septic shock is that the syndrome is caused by the overwhelming reaction of the immune system to infectious agents, thereby resulting in a profound release of inflammatory mediators into the bloodstream and into tissues. Accordingly, it is believed that these mediators are the direct cause of organ and tissue injury.

Septic shock typically advances in two stages. First, patients demonstrate symptoms characteristic of vasomotor effects that follow cytokine and ACTH/endorphin release, kallikrein/kinin system activation, and histamine release induced by bacterial cell wall components or toxins. Thereafter, the resultant circulatory changes and capillary damage cause microvascular dysfunction, a fall in intravascular blood volume, decline in cardiac output, disseminated intravascular coagulation, and organ dysfunction. Cytokines, therefore, are involved in the generation of sepsis and septic shock. Cytokines are intercellular mediators. For example, cytokines play a role in the generation of an immune response, such as in an immune response to an infection or infectious organism.

Capillary leak syndrome (CLS) occurs as a side effect of cardiovascular surgery in that cytokines and anaphylatoxins are generated as a consequence of the blood oxygenation procedures employed during surgery. Virtually all children, and 50-75% of adults, suffer from this syndrome during or after cardiovascular surgery. The vascular injury and organ impairment produced by CLS resemble the impairments produced in septic shock.

In general, conventional therapies for septic shock and CLS require intensive monitoring and care. Typically, the therapies are directed to the maintenance of blood pressure, organ perfusion and oxygenation. These therapies often involve assisted ventilation, and often include volume replacement with plasma expanders such as 5% albumin, isotonic saline, or lactated Ringer's solution. Sufficient volume is provided to raise the pulmonary capillary wedge pressure to the high normal range. When simple volume replacement is not sufficient, vasopressor compounds such as dopamine, dobutamine, or norepinephrine may be used. Antiinflammatory drugs such as methylprednisolone, sodium succinate and antiprostaglandins, for suppression of inflammatory damage, may be used as needed. Other therapies include antimicrobial agents, corticosteroids, anticoagulants, and diuretics.

The results achieved by these septic shock and (CLS) treatments are not always completely satisfactory. Antibiotic therapy may exacerbate toxic shock by inducing the release of bacterial cell wall materials and toxins. Vasopressors do not ameliorate shock or capillary wall damage. Volume replacement may result in edema and cardiac complications.

Acute renal failure is broadly defined as a rapid deterioration in renal function sufficient to result in accumulation of nitrogenous wastes in the body. The causes of such deterioration include renal hypoperfusion, obstructive uropathy, and intrinsic renal disease such as acute glomerulonephritis.

Release of large amounts of myoglobin into the circulation is a common cause of acute renal failure. A number of conditions may cause myoglobinuria, usually with the acute onset of weakness or paralysis: Crush injury or infarction of a large mass of muscle; excessive muscular contraction; acute idiopathic polymyositis and viral myositis; or, drugs and toxins.

Frequently, rhabdomyolysis and myoglobinuria are due to extensive trauma with crush injuries. However, nontraumatic rhabdomyolysis associated with increased muscle oxygen consumption (heat stroke, severe exercise, and seizures), decreased muscle energy production (hypokalemia, hypophosphatemia, and genetic enzymatic deficiencies), muscle ischemia (arterial insufficiency, drug overdosage with resultant coma and muscle compression), infections (influenza), and direct toxins (alcohol) also can produce rhabdomyolysis resulting in acute renal failure.

Thus, with any disease that results in rapid destruction of a large mass of striated muscle, myoglobin and other muscle proteins enter the bloodstream and may appear in the urine, whereupon the urine becomes dark red or burgundy colored. Myoglobin may be separated from hemoglobin by spectroscopy or radioimmunoassay. When myoglobinuria is severe, renal damage may ensue and lead to anuria.

The exact mechanism whereby myoglobinuria results in acute renal failure is uncertain. Most likely, the mechanism of renal damage is not simply a mechanical obstruction of the tubules by precipitated myoglobin. Typically, the treatment for acute renal failure corresponding with myoglobinuria addresses the underlying cause of the myoglobinuria, if remedial. The treatment for anuria would be the same as with anuria following surgical shock.

Some authors have discussed the possibility that whole blood, or at least certain blood components, be extracorporeally treated to preferentially remove certain materials present in the blood. Some authors have also addressed the use of silica-based materials in those treatments. However, all proposed silica-based materials have been chemically modified silica. The chemical modifications are directed to providing a silica material that will not lead to blood coagulation, and resultant clogging/failure of the silica column. It was believed that a device that utilized unmodified silica would lead to failure, since chemical modifications on the silica were understood to be necessary to accomplish the desired results. Chemical modification of silica is, however, an intricate process that adds significantly to the cost of the resultant materials. Further, the chemically modified silica materials have not been fully successful at providing the desired dual result of removing selected factors from blood, while avoiding clotting within, and resulting failure of, the silica-containing device. Accordingly, there has been a need for a cost efficient and effective silica material for use in removing selected factors from a patient's blood.

SUMMARY OF THE INVENTION

The present invention addresses treatment of whole blood or plasma to lower the circulating levels of certain unwanted selected factors (such as cytokines, complement molecules, serotonin, histamine, cholesterol molecules, myoglobin or a component thereof, angiogenesis factor, or pharmaceuticals) in the blood by physical or physico-chemical adsorption of those factors on a specially treated silica-based adsorbent. In a preferred embodiment the treatment is extracorporeal, alternatively the treatment may comprise an in-dwelling catheter. In accordance with the invention, various toxic effects of the selected factors are avoided or lessened. Furthermore, should the invention be used in conjunction with the other treatments, the extent of such other treatments will be lessened. It is also within the scope of the invention that the method may be used on components of whole blood.

Pretreated silica forms an aspect of the invention, as does a device containing the silica. A preferred method of the invention is a process for lowering the circulating levels of selected factors such as cytokines, lymphokines, or other low molecular weight inflammatory mediators such as histamine, serotonin, anaphylatoxins, etc. in whole blood, by contacting that blood with a porous silica material which has been treated with a silica pretreating agent. Cytokines play an important role in producing the clinical signs and symptoms of sepsis and septic shock. Accordingly, cytokines are comprised within the variety of selected factors and are a preferred selected factor to be removed in accordance with the present invention. Thus, the process is desirably used for the prevention or treatment of septic shock or other diseases caused by the selected factors. An object of the invention is to process blood to effect a clinically favorable response. In addition, the invention produces less than 1% hemolysis. Alternatively, the invention has also been used to remove pharmaceuticals from patient's blood.

Preferably, the silica is amorphous, granular, not chemically modified, and retained in a binder such as a matrix, or retained within a device so as to prevent loss into the patient. An anticoagulation regimen is also set forth which is advantageously used in conjunction with the invention.

BRIEF DESCRIPTION OF THE DRAWINGS

FIGS. 1A and 1B show schematic diagrams of a system in which the inventive process may take place.

FIG. 4D shows percent hemolysis of citrated whole blood after recirculating 10–12 times through a test column. FIGS. 4A–D show the results from experiments wherein silica column was not pretreated, but merely flushed with saline before use.

DETAILED DESCRIPTION OF THE INVENTION

Figure 1B:
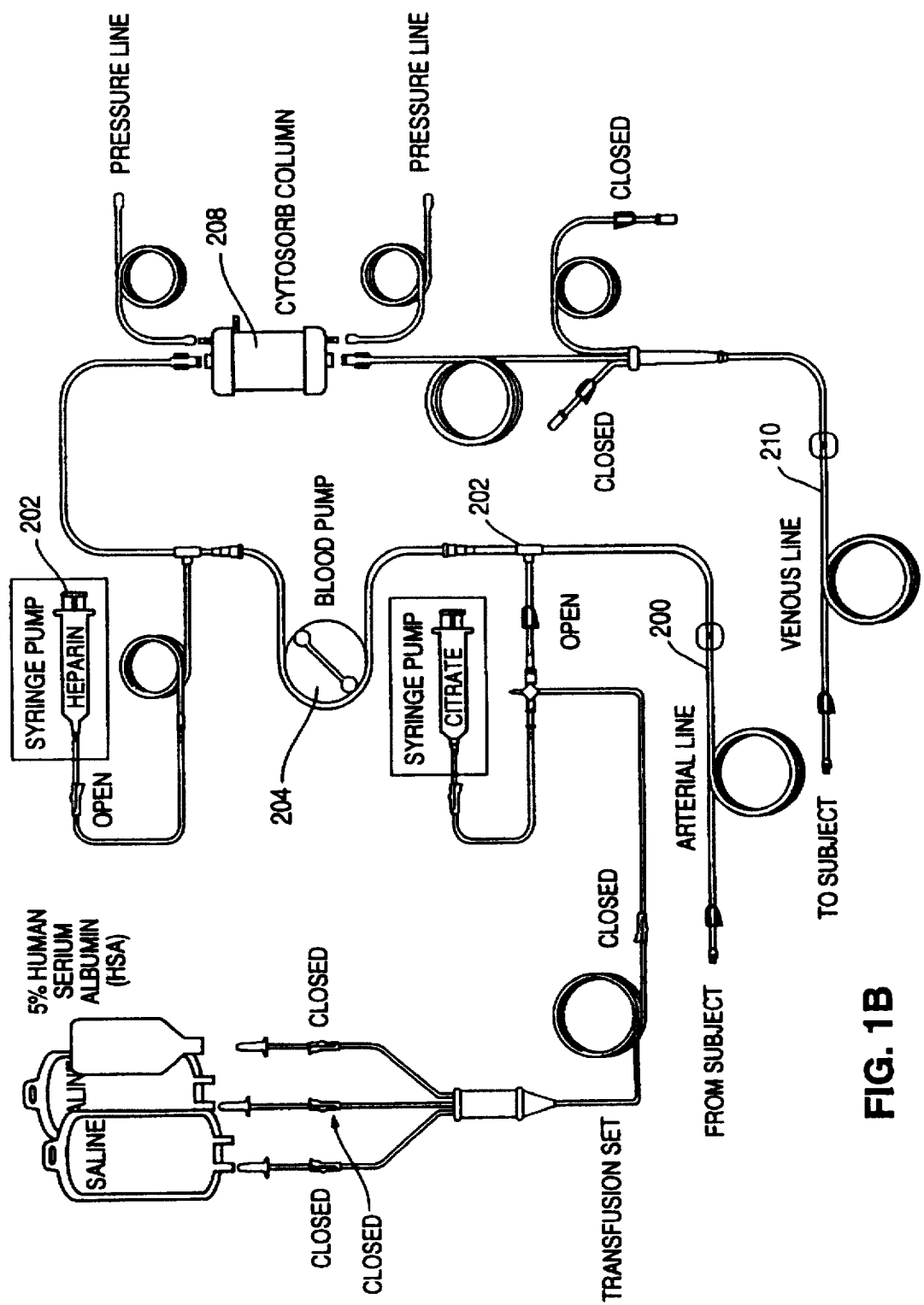

The present invention relates to the removal of selected factors comprising cytokines, lymphokines or other low molecular weight inflammatory mediators such as histamine, serotonin, or anaphylatoxin, from whole blood or plasma. Preferably, the invention is used for the treatment of septic shock or capillary leak syndrome. Accordingly, a patient's whole blood or plasma, is contacted with a composition comprising silica and a surface treatment material, preferably human serum albumin (HSA). In a presently preferred embodiment the treatment is extracorporeal, alternatively the treatment may comprise an in-dwelling catheter. In a preferred form of the invention, the silica used of the composition of the invention is not chemically modified. Further, the composition is understood to result in substantially no chemical modification of the silica it comprises.

In particular, the present invention is used to lower the content of cytokines, cytokines such as are found in conjunction with septic shock or capillary leak syndrome (CLS). The invention is also used to lower the concentrations of other bioactive materials such as histamine, serotonin, and anaphylatoxins (C3a and C5a) and various other substances addressed, e.g., in FIGS. 2A, 2B, 3A and 3B.

The method of the present invention will be used to lower the IL-1 and IL-8 content in the blood of a patient experiencing CLS. Accordingly, the invention may be utilized to control the incidence and severity of capillary leak syndrome.

Similarly, the process may be used either alone or in conjunction with various forms of chemotherapy to lower the concentration of tumor necrosis factor in a patient's blood.

Silica Adsorbent

The preferred silica suitable for use in this invention comprises chemically unmodified amorphous silica suspension, typically termed silica gel. It is believed that silica parameters of surface area and pore size determine suitability of the silica in the invention. Preferably, the silica has a surface area between about 150 m$^2$/g and 1000 m$^2$/g, more preferably between 200 m$^2$/g and 600 m$^2$/g. Additionally, it is preferred that the silica has between 0.5 cc/g and 2.5 cc/g of porosity. It is believed to be more preferable that the silica has porosity between 0.8 cc/g and 1.5 cc/g. Desirably, the silica particles have an average diameter between about 50 and 250 microns for treatment of septic shock, and up to 1 mm for other applications. Accordingly, PQ10150 silica obtained from PQ, Inc., Conshohocken, Pa. has been found to be suitable for use in the invention.

The preferred amorphous silica used in this composition is particulate. The particulate silica may be in any of a variety of physical shapes (e.g., granular or spherical). By "granular silica" is intended a silica from crushed silica. By "spherical silica" is intended particulate silica that has been produced to have a substantially rounded contour. However, the shape and size should be selected to allow free flow and to prevent, or at least lessen, hemolysis during the passage of whole blood through the silica bed. Although any shape is permissible, granular silica has been used to advantage.

Granular silica gel has been used to good effect when the bed is designed so that the superficial velocity of the blood through the device of the invention is less than about 2.5 cm/sec. The devices utilized herein were approximately 9.5 cm in diameter. Preferably, when used to remove cytokines in the treatment or prevention of septic shock, the flow rate is about 100–500 ml/min, which corresponds to a superficial velocity of between 0.02 cm/sec and 0.11 cm/sec. The flow rate range for the treatment or prevention of capillary leak syndrome is 1–10 liters/min, which corresponds to a superficial velocity of 0.23–2.34 cm/sec.

It is believed that there is a relationship between silica pore diameter and the protein species adsorbed. In accordance with this relationship, we have found that silica having a mean pore diameter of 30 Å to 300 Å is suitable for the prevention or treatment of septic shock (whether from gram-positive or gram-negative bacteria), and that a mean pore diameter between about 60 Å and 200 Å is especially suitable.

Pretreatment of Silica Adsorbent

Unexpectedly, we have found that pretreating the silica particles by contacting them with 5% HSA provides a significant lessening of platelet activation and clotting. Accordingly, undesired platelet loss is reduced. Pretreated silica has been obtained as follows.

A cylindrical column with a diameter of approximately 3.2 cm was prepared so that it contained 10 grams of silica. After the appropriate tubings were attached, the column was flushed with 200 to 300 milliliters of sterile 0.9% sodium chloride USP injectable saline at 50 milliliters per minute, to remove air and any small particles from the column. The silica column was then treated for 10 to 15 minutes with a sterile injectable 5% human serum albumin prepared by diluting sterile injectable 25% human serum albumin with sterile 0.9% sodium chloride USP injectable saline to a 5% solution. Pretreatment of the silica was accomplished by either of two protocols. In one protocol, the columns were flushed with 200 to 300 milliliters of the injectable 5% human serum albumin at 50 milliliters per minute and then left to stand for 10 to 15 minutes (typically the amount of time it required to set up the citrated or heparinized blood for processing or to connect a patient to the device). Alternatively, pretreatment was accomplished by recirculating the injectable 5% human albumin through the column for 10 to 15 minutes. Both protocols for obtaining pretreated silica were equally suitable, and were used interchangeably throughout the following experiments.

Various quantities of a composition in accordance with the invention can be prepared. For example, a preferred composition in accordance with the invention can be obtained with larger silica-containing columns. A composition of the invention has been prepared in silica-containing columns that were approximately 9.5 cm in diameter, and which each contained 145 grams of silica; and in columns approximately 3.7 cm in diameter which each contained 20 grams of silica.

To prepare the composition in the columns containing 145 gm or in the columns containing 20 gm of silica, the columns were first flushed with 0.9% sodium chloride, USP injectable saline. The columns containing 145 gm were flushed with 10 liters of the 0.9% sodium chloride, USP injectable saline. The smaller columns containing 20 gm were flushed with two liters of the saline solution. For either column size, the saline was provided at a flow rate of 100 to 500 milliliters per minute. The saline solution was provided along with citrate, at a flow rate of 5 ml/min, in order to remove air and small particles. Thereafter, sterile injectable 5% human serum albumin was pumped through the flushed devices at 100 milliliters per minute, along with 5 milliliters per minute of Acid Gitrate Dextrose, NIH Formula A (ACDA), in order to displace the saline and to pretreat the device with albumin. For the device containing 145 gm of silica, 1 liter of the 5% human serum albumin was used. For the device containing 20 gm of silica, 0.5 liter of the 5% human serum albumin was used. The devices were then allowed to stand for 10 to 15 minutes, approximately the time it took to properly connect an animal subject to a device for processing. As described above, pretreatment of silica can occur by continuous recirculation of the pretreating agent through the silica bed, or by allowing the pretreating agent and silica to stand for a significant period of time.

An HSA concentration of 1% to 25%, preferably 2.5% to 5.0%, is suitable for use in creating a composition with the silica granules. However, any reasonably prudent concentration of HSA in a carrier will be acceptable.

It was also found that silica pretreated with heparin was useful in the invention. The HSA and heparin pretreatment protocols are analogous. For the pretreatment of silica with heparin, a 10 U heparin/1 ml saline solution was used instead of the 5% HSA. The heparin-saline solution was prepared by combining sterile 0.9% sodium chloride USP injectable saline with sterile injectable heparin, to arrive at a solution with a concentration of 10 units of sterile injectable heparin per milliliter. Accordingly, heparin-pretreated silica was obtained by flushing a column having a diameter of approximately 3.2 cm and containing 10 grams of silica with 260 to 300 milliliters of a heparin-saline solution. After flushing the device, the device (containing the heparin-saline solution) was left to stand for 10 to 15 minutes.

To prepare a composition in accordance with the invention, silica granules may be precoated and maintained until ready for use, or the granules may be pretreated in a column just prior to a blood treatment session. Pretreatment of silica can occur by continuous recirculation of the pretreating agent through the silica bed, or by allowing the pretreating agent and silica to stand for a significant period of time. By "significant period of time" we mean at least about 10–15 minutes, often the time it takes to completely connect a subject to the device.

Medical Device

The preferred particles of amorphous silica can readily be placed in a container for the purpose of preparing a device in accordance with the present invention. The container can be constructed of any material which can readily undergo steam, chemical, or gamma-irradiation sterilization. For instance, glass, polycarbonate, polystyrene, polymethylmethacrylate, polyolefins such as polyethylene and polypropylene, are all suitable.

Various ways of retaining or immobilizing the silica within a container are available. For instance, the silica may be placed between layers of a retaining filters, or placed within a porous solid matrix. The solid matrix immobilizes the silica while simultaneously permitting flow of blood and contact with the silica. As is readily apparent to one of ordinary skill in the art, a wide variety of structures are available for providing suitable blood/silica contact, structures which do not cause significant hemolysis. Prudent use of additional filters to retain the silica particles in their container is preferred. The pretreated and immobilized silica may be contacted with the blood in a variety of ways.

An embodiment of a device suitable for use in the practice of this invention is shown in schematic form in FIG. 1A. As shown in FIG. 1A, blood enters through line 100 and passes through pump 102. Pump 102 supplies sufficient flow rate and pressure to the discharged blood to allow the blood to flow through silica bed 104 and return to the body at an appropriate pressure. Silica bed 104 has pressure monitoring devices (106 and 108), adjacent its inlet and its outlet, respectively. Accordingly, the silica bed 104 is monitored for blockage or incipient blockage. The blood, once it passes through silica bed 104, may be returned to the body through line 110. Advantageously, the total volume of the device should be less than about 700 ml for use on human patients.

Although a cylindrical silica bed is depicted in FIG. 1A, silica beds of any other shape capable of functioning in the manner described herein may be used. The length-to-diameter ratio of a silica bed should be selected so as to minimize any pressure drop along the silica bed so as to ensure that shear rates remain below the known values that correlate with cellular damage or destruction. The pressure drop along a silica bed (and thus the increase in shear rate) is directly proportional to the length of the bed. However, mitigating against use of a short bed is the fact that clearance of a substance from the blood increases with a longer bed.

The capability of the composition to adsorb can be assessed by experiments in which a test solution (such as whole blood or plasma) is contacted with the composition at a constant temperature. The data generated from such an experiment can be used to determine an equilibrium constant (K), according to which the capacity of the composition is determined. An equilibrium constant (K) is defined in units of (ml solution/g composition). The capacity of a composition provides a way to estimate the mass of the composition required to remove a certain quantity of material from solution. This approach was used to estimate the mass of silica required to remove cytokines implicated in sepsis and septic shock in humans.

Batch experiments were conducted (at 37° C.) by contacting approximately 0.2 grams of silica with solutions of known concentrations of sorbate (cytokines and complement). Radio-labeled cytokines and complement were prepared in 5% HSA buffered (pH 7.2) with sodium bicarbonate (25 mM) and tonicity adjusted with sodium chloride (150 mM). After an equilibration period of 40 minutes (considered sufficient to ensure equilibrium between the solid and liquid phases), each sample container was centrifuged (to cause the silica to sediment) and a sample of the supernatant removed and assayed. Table 1 shows typical values (averaged from triplicate experiments) for the equilibrium constants (K) of the cytokines and complement using non-irradiated silica. Equilibrium constants were determined according to known methodologies. It is clear from Table 1 that circulating cytokines will be adsorbed by the silica at different rates. The effect of gamma irradiation on K was examined using two cytokines: interleukin-8 (IL-8) and tumor necrosis factor (TNF-α). These results are shown in Table 2, and are the average from experiments performed in triplicate with each of three different lots of silica. Table 2 indicates that gamma irradiation does not affect the capability of the silica to adsorb proteins.

TABLE 1

Equilibrium Constants (K) Of Cytokines.
(Non-Irradiated Silica & Buffered 5% HSA Solution)

| Protein | Equilibrium Constants (K) (ml solvent/g sorbent) |
|---|---|
| C3a Des Arg (complement) | 51.27 |
| TNF-α | 63.42 |
| Interleukin-6 (IL-6) | 33.0 |
| Interleukin-8 (IL-8) | 137.23 |
| Interleukin-1α (IL-1α) | 14.1 |

TABLE 1-continued

Equilibrium Constants (K) Of Cytokines.
(Non-Irradiated Silica & Buffered 5% HSA Solution)

| Protein | Equilibrium Constants (K) (ml solvent/g sorbent) |
|---|---|
| Interleukin-1β (IL-1β) | 10.9 |
| Gamma Interferon (γ-IFN) | 2.1 |

TABLE 2

Equilibrium Constants (K) Of TNF-α & IL-8
(Irradiated & Non-Irradiated Silica & Buffered 5% HSA Solution)

| Protein | Equilibrium Constants (K) (ml solvent/g sorbent) Non-Irradiated Silica | Equilibrium Constants (K) (ml solvent/g sorbent) Irradiated Silica |
|---|---|---|
| TNF-α | 63.42 | 71.74 |
| IL-8 | 137.23 | 145.83 |

Using the K value for TNF-α for example, it was possible to estimate (by use of known equations) the minimum mass of silica required to lower the concentration of TNF-α to sublethal levels from the plasma of a subject. For example, for an adult human subject, one would start with a blood circulating level of TNF-α of 1 ng/ml; the reduction would be approximately 50%. For illustrative purposes, the plasma component of the volume of blood corresponding to a typical 70 kg subject having a 45% hematocrit was employed. Accordingly, the minimum mass of silica required to lower the concentration of TNF-α to sublethal levels from the plasma of such a subject is approximately 50 grams. A device in accordance with the present invention, the AIS Cytosorb™I-A device (Applied Immune Sciences, Inc., Santa Clara, Calif.) contains 145 grams of silica. The extra silica is included for removal of TNF-α stored in the extravascular compartment, and any newly generated TNF-α, as well as to accommodate removal of other selected factors (e.g., IL-1, IL-6, etc.). However, the adsorption of materials is not competitive. Thus, even for the calculated minimal amount of 50 gm of silica, TNF-α as well as other selected factors will be adsorbed.

Analogous studies were done using juvenile pigs of 2–10 kg in mass. Using the blood volume from a typical juvenile pig, and applying equilibrium isotherm calculations analogous to those used for a typical 70 kg subject (discussed above) a smaller yet dimensionally similar device was developed. The smaller device was approximately 3.7 cm in diameter, and contained 20 grams of silica. Again using the K value for TNF-α, equilibrium isotherm calculations indicated that approximately 5 gm of silica were required to reduce TNF-α to sublethal levels in a juvenile pig subject. For juvenile pig subjects, a starting blood circulating level of TNF-α was 1 ng/ml; the reduction of TNF-α would be to approximately 50% of the starting value. Although approximately 5 gm of silica were required to reduce TNF-α to sublethal levels, 20 grams of silica were used in the smaller device, in order to accommodate removal of TNF-α stored in the extravascular compartment, any newly generated TNF-α, as well as to accommodate removal of other cytokine species.

Since the larger and smaller devices were dimensionally similar, the physical parameters relating to flow stress were similar, and thus safety data were comparable for both devices.

The Process

By employing the process of the present invention, we have found that the device discussed above is excellent for adsorbing proteinaceous molecules. We have noted that the device removes significant levels of serotonin; histamine; anaphylatoxins, such as complement molecules C3a and C5a; and cytokines such as interleukin-1 (IL-1), interleukin-6 (IL-6), and interleukin-8 (IL-8); interferons; or tumor necrosis factor (TNF) from whole blood. Although it is preferred that the invention be used to treat whole blood, it is also suitable for treating blood components, such as plasma.

The equilibrium isotherm studies, addressed above, indicated that a device containing 145 gm of silica (adsorbent), has approximately three times the capacity needed to effect a clinically meaningful reduction of targeted cytokines from a typical 70 kg human subject. Thus, a device comprised of a clear plastic cylindrical housing with an internal diameter of approximately 9.5 cm, an internal volume of approximately 600 milliliters, and containing 145 gm of silica was used for a series of experiments. The device was used in a process according to the invention, to treat young healthy (50–60 kg) swine which were provided with either a citrate or a combined citrate and heparin anticoagulation regimen.

Accordingly, after a 600 milliliter device was physically set up, the device was flushed with ten liters of sterile 0.9% sodium chloride USP injectable saline at 100 to 500 milliliters per minute and 5 milliliters per minute of Acid Citrate Dextrose, NIH Formula A (ACDA), to remove air and small particles.

To accomplish pretreatment of silica, the device was then flushed with one liter of sterile injectable 5% human serum albumin (prepared as described above) at 100 milliliters per minute, along with 5 milliliters per minute of ACDA to displace the saline, and to fill the column with the HSA solution. The column was left to stand while the animal was being prepared for blood processing, typically on the order of about 10–15 minutes.

After completion of the silica pretreating procedure, the subjects were prepared for blood processing. The subjects were first given a bolus injection of 100 units of sterile injectable heparin per kilogram of body weight. After the bolus heparin injection, the arterial and venous lines of the device were attached and secured to vascular access sites on the subject. Injectable heparin and calcium solutions, and any fluid pumps were also attached to their appropriate ports.

Blood processing was then begun. The blood processing procedure utilized an initial flow rate of 100 milliliters per minute of whole blood obtained from one of the central vascular accesses; while 5 milliliters per minute of ACDA, and 40 units of heparin per kilogram of body weight per hour were input through the arterial line, and 100 mg per kilogram per hour of calcium chloride was input through another peripheral venous or central venous access port. After 30 minutes of flow at 100 milliliters per minute, the flow rate was increased to 300 milliliters per minute for the duration of the study. After the blood passed through the device, it was returned to the subject in a continuous circuit through another access port.

Throughout the procedure, blood activated clotting time and calcium were checked periodically. If the clotting time approached or was less than 200 seconds, additional heparin was given by intravenous bolus injection to prolong the clotting time. If the ionized calcium came below 0.8 millimole per liter, the subjects were given additional calcium. As addressed below in the Examples section, twelve animals were successfully treated with this device and process without significant clotting or adverse events.

Analogous studies were done using juvenile pigs of 2–10 kg in mass. A smaller device (discussed above), containing 20 grams of silica, was used to study the juvenile subjects. The procedure for preparing the smaller device corresponded to the procedure described for the larger device, however smaller volumes of saline and silica pretreating solutions were used. In the studies with smaller devices, two liters of saline flushing solution, and 0.5 liter of silica pretreating solution were used. Additionally, lower flow rates were used than had been employed with the 600 ml. device. The blood flow rates for the smaller device ranged between 30 to 60 milliliters per minute. However, for subjects treated with the smaller device, the citrate anticoagulant was concentrated trisodium citrate in equivalent citrate quantities (0.33 to 1.0 milligram per milliliter of blood) as the ACDA. Concentrated trisodium citrate was used in order to maintain the volume of fluid infused into the 2–10 kg subjects within acceptable levels. The 2–10 kg subjects could not tolerate the fluid volume required to anticoagulate with an ACDA solution. The dose of heparin used was the same as for subjects treated with the larger device. Calcium chloride was not needed because the subjects treated with the smaller device were able to metabolize citrate and maintain adequate blood ionized calcium. As addressed below in the Examples section, twelve subjects were also successfully treated in this manner.

FIG. 1B shows a typical system in which the inventive process may be carried out. Blood from the patient is introduced into the system by arterial line (200). The blood flows by junction (202) where it is mixed with any necessary adjuvants, such as saline, sodium citrate, heparin, or the like, and proceeds to blood pump (204). If desired during the process, heparin can also be added from a heparin pump (206). Furthermore, if heparin is the desired silica surface treatment agent, heparin from heparin pump (206) can be used to pretreat the silica in silica column (208). After blood has passed through silica column (208), the blood is then returned to the patient via venous line (210).

Generally, anticoagulated blood is used with the present invention. When anticoagulating blood, however, one cannot safely achieve anticoagulation to a degree that absolutely assures that no clotting will occur; were the blood to be anticoagulated to this level, the patient would tend to undergo bleeding diatheses. Accordingly, when blood is anticoagulated within limits that are safe for the patient, clotting may occur within the passageways leading to or from the device, or within the device itself. Clotting may be significant enough to block the flow through the device. More commonly, clotting will not entirely block the device, it will, however, lead to platelet depletion.

Accordingly, an anticoagulation regimen is advantageously utilized in conjunction with the process of the invention. In most instances, we have found it highly desirable to include anticoagulants such as citrate, heparin, or a combination of citrate and heparin, to the system to manage any clotting that may occur. Heparin may be added both as a bolus at the beginning of the treatment and continuously during the treatment step. Systemic heparin levels suitable for maintaining an activated coagulation time of >200 seconds is desired. Alternatively, citrate levels in a ratio of 1:10 to 1:60 (Acid Citrate Dextrose, NIH Formula A (ACDA): whole blood) may also be maintained in the system. These citrate levels are equivalent to 0.3 to 1.5 mg citrate/ml blood. The citrate or citrate equivalent is usually added by continuous addition.

The invention is further illustrated by, but not limited to, the following examples.

EXAMPLES

Example 1

Selected factors are released into the plasma component of blood when they are produced. In order to obtain more definitive assay values, plasma was used in this experiment rather than whole blood. Because of the cells in whole blood, studies with whole blood would tend to produce confounding background values. For example, blood cells have the capability of producing selected factors, such as cytokines. Additionally, many cells from whole blood have receptors for selected factors on their surfaces. These receptors can lead to the effective compartmentalization of such factors, further confounding the accuracy of assay values. If blood cells either produce or attach selected factors, whole blood assays concerning such factors would potentially be skewed.

Figure 2A:
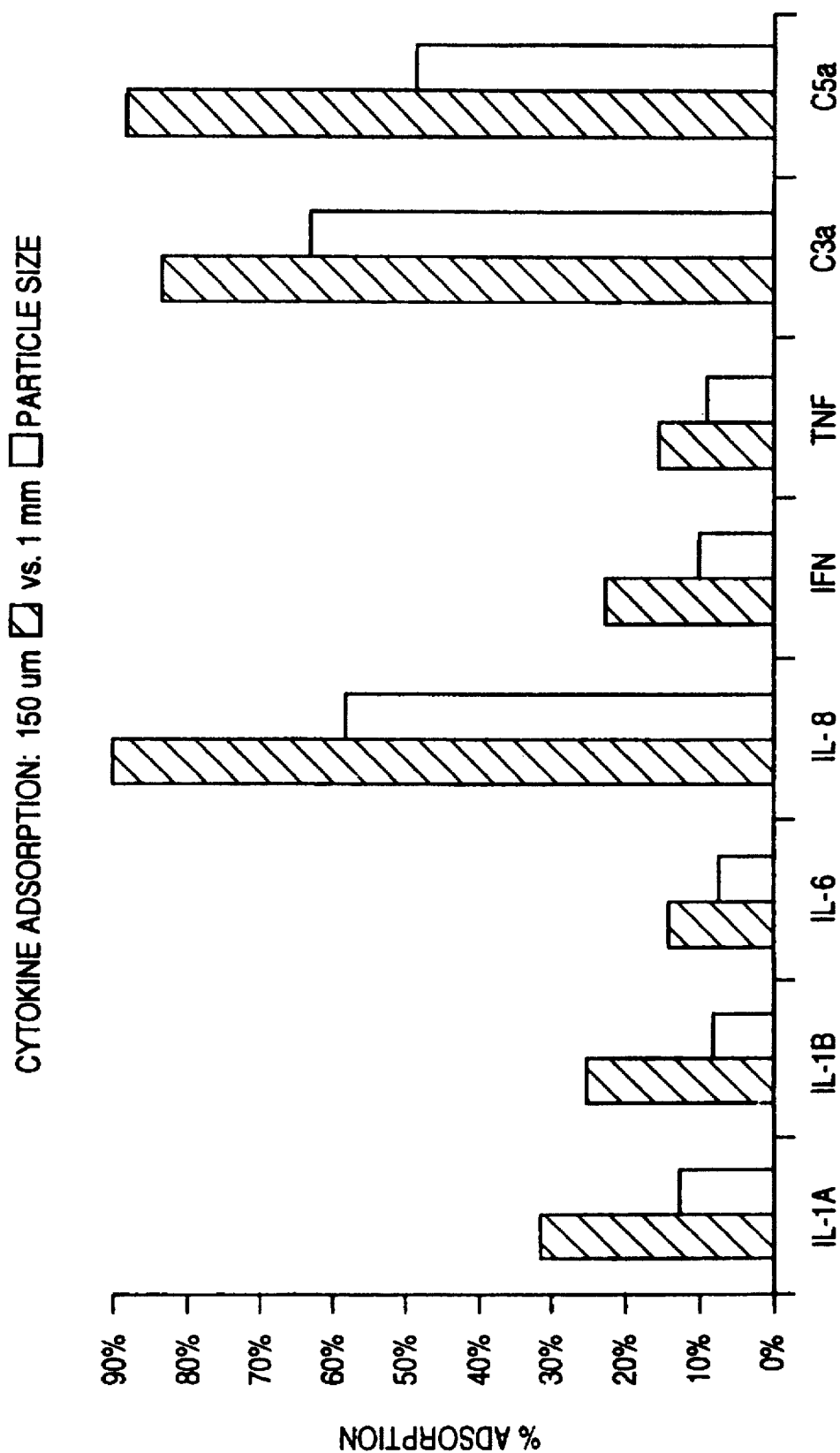
FIG. 2A shows the results of cytokine adsorption as effected by silica particle size.
Figure 2B:
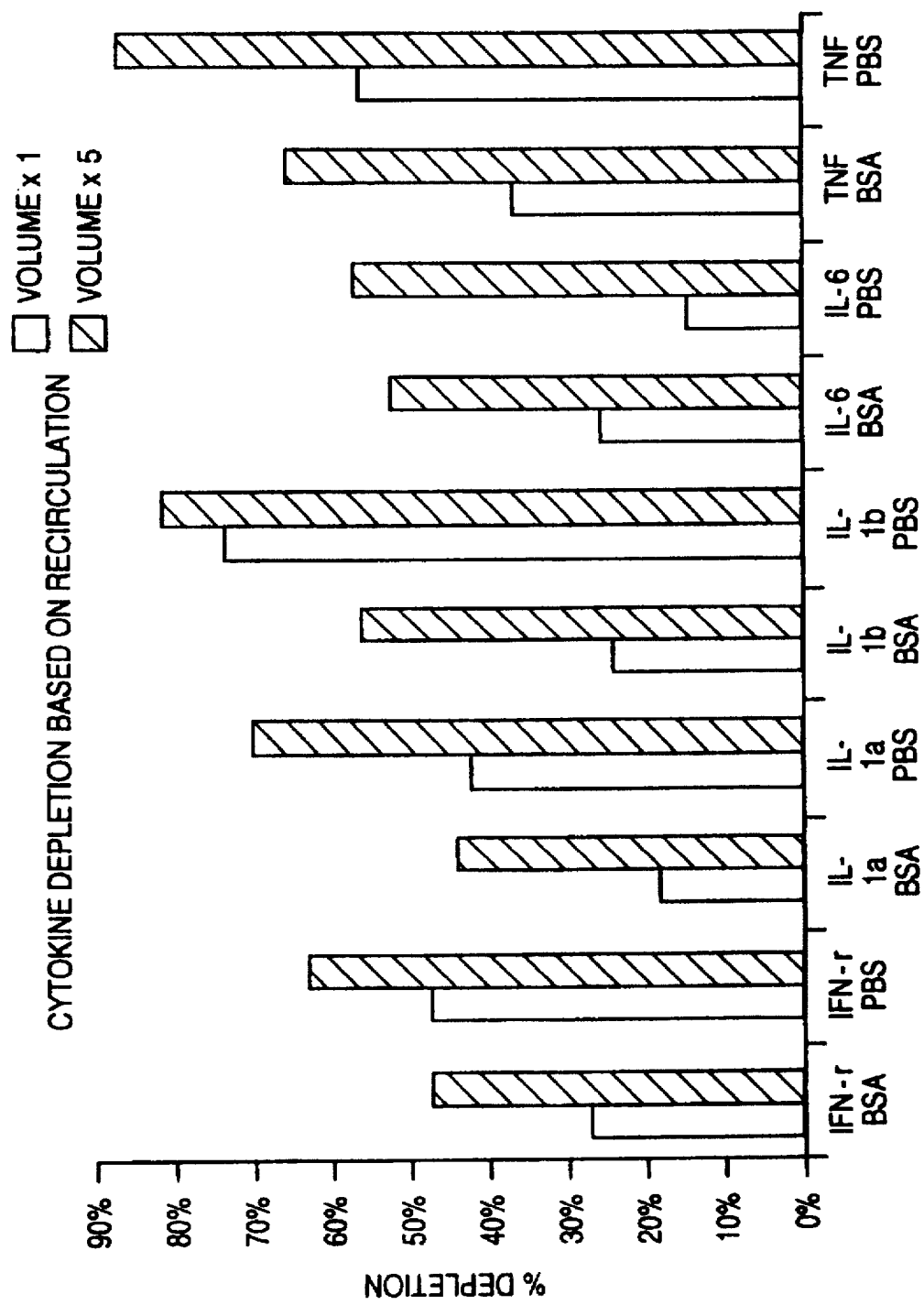
FIG. 2B shows the results of cytokine adsorption based on recirculation through a device in accordance with the invention.

In this example, a small column of silica (0.9 g) was used to treat normal plasma spiked with different amounts of cytokines and complement molecules. The plasma, in each instance (40 ml), was passed once through the column at a rate of 3.1 ml/min. All of the C3a and C5a were removed in this one-pass study. More than 80% of IL-1 and 50% of IL-6 were removed. FIG. 2A depicts the results of studies comparing the adsorption of various selected factors, based on the use of devices that have 150 um and 1 mm silica particles. For each selected factor analyzed, a higher percentage of adsorption was obtained by utilizing the smaller particle size. FIG. 2B exemplifies that selected factors were removed in greater amounts when blood plasma was recirculated through a device of the invention. This finding is especially relevant for clinical applications, since blood recirculation will likely be the norm in these settings.

Example 2

Figure 3A:
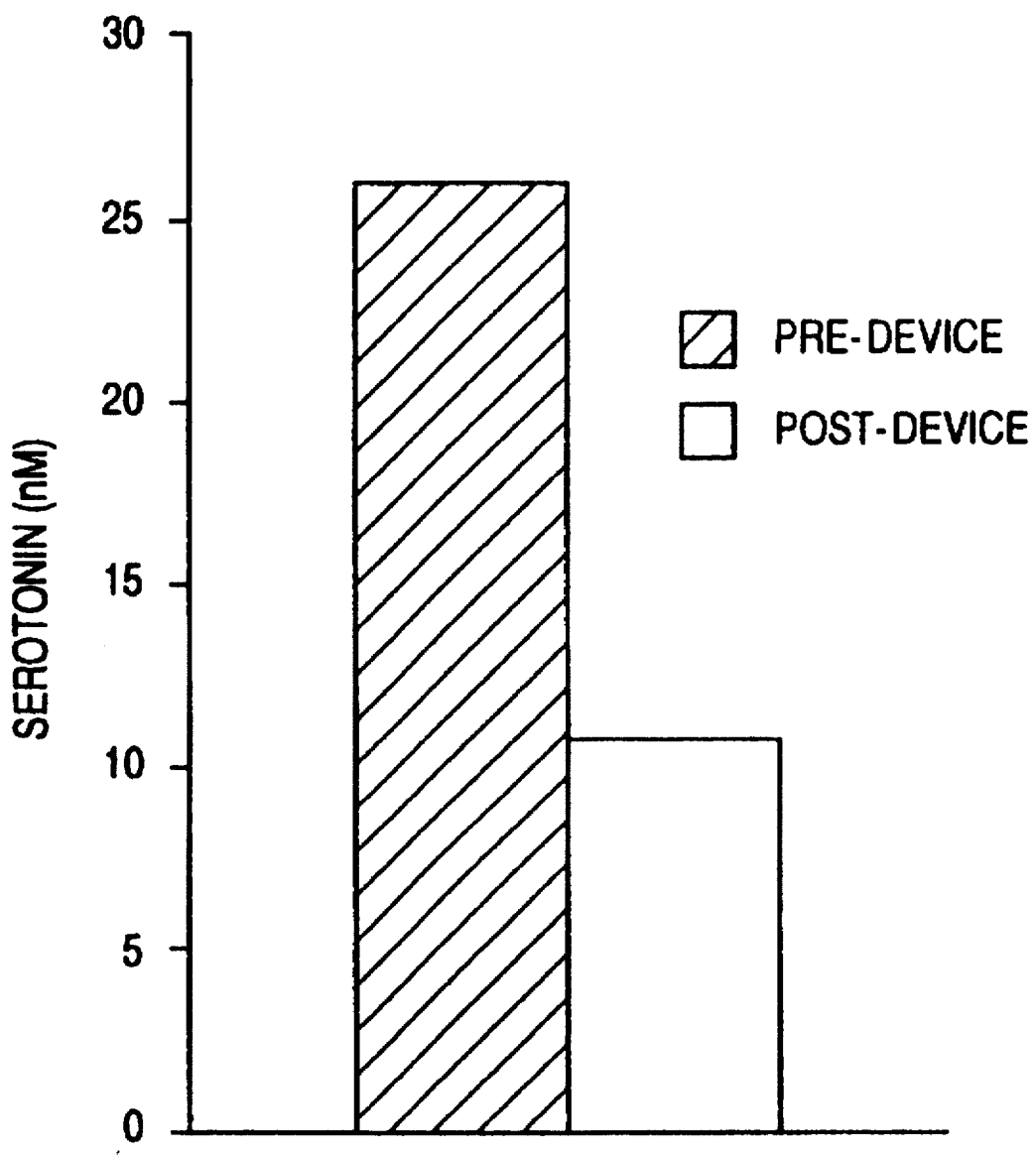
FIGS. 3A and 3B show the removal of serotonin and histamine, respectively, from blood plasma by use of a silica column.
Figure 3B:
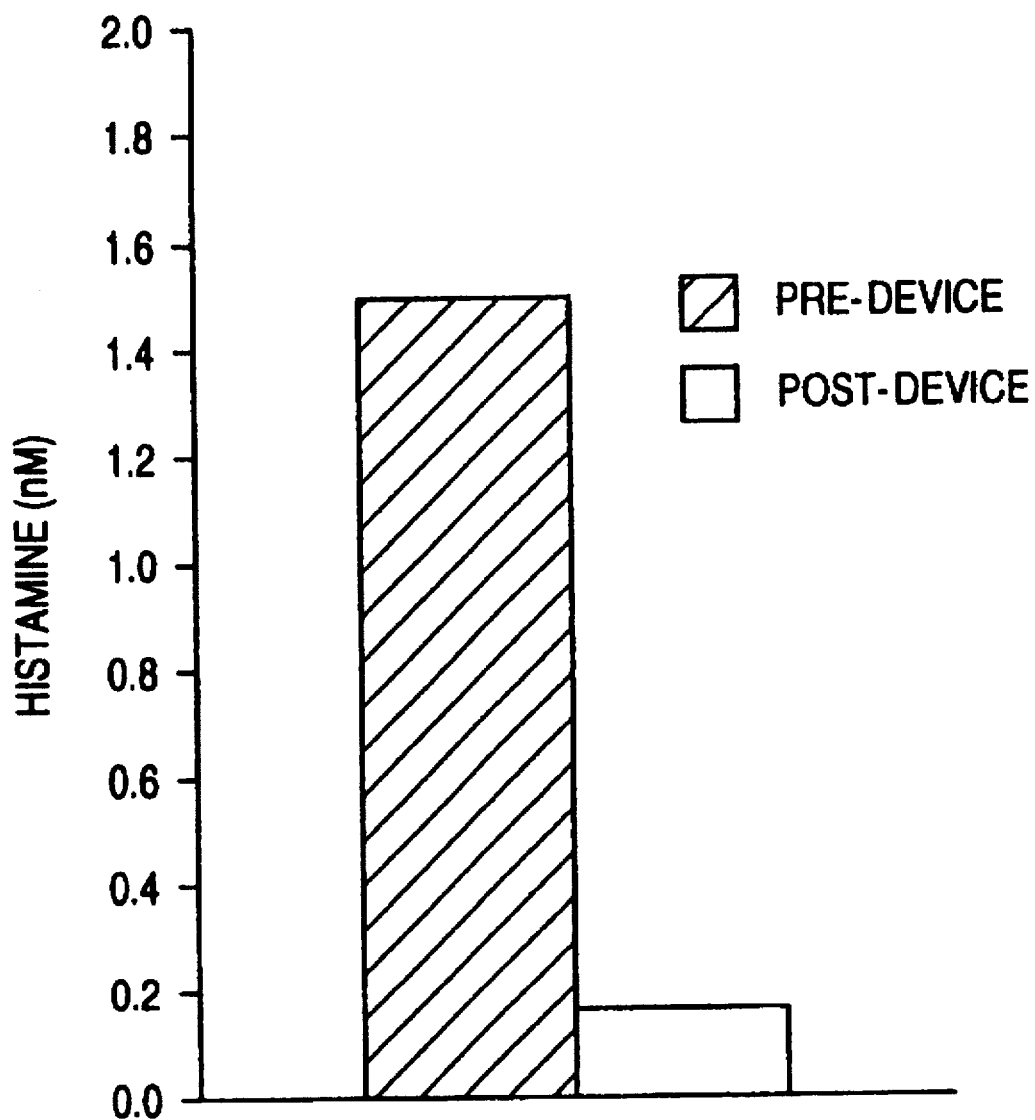

In this example, two factors implicated in septic shock, serotonin and histamine, were removed from the blood plasma of a patient undergoing a therapeutic plasmapheresis. The patient's blood was separated into its cellular and plasma components by centrifugation. In accordance with treatment regimens known in the art, the cellular component, concentrated by centrifugation, was combined with physiologic solutions and returned to the patient. In standard practice, the plasma component is then disposed of. However, in this example, the plasma component was diverted to a saline flushed silica column before disposal. Serotonin and histamine in the sample were measured both before and after passage through the silica column. The resulting data (FIG. 3A) showed that the concentration of serotonin was cut by approximately 60%. As shown in FIG. 3B, the histamine level was cut by almost 90%.

Example 3

In this example, devices using granular silica were tested using fresh whole blood (anticoagulated with citrate) to determine the loss of white and red blood cells, as well as loss of platelets. Various test devices were used. These devices had different filters, contained either 70- or 135-micron diameter silica particles, and contained either 0, 5 or 10 g silica. A device without silica in its column was used as a control.

Initially, the device was flushed with saline. Then, blood was recirculated at a volume flow rate of 50 ml/min for the first 120 minutes. Thereafter, the flow rates were increased to 100, 200, 300 and 437 ml/min; at 120, 127, 134, and 140 minutes, respectively. Samples were taken at time 0, and at 15 minute intervals until 120 minutes. Thereafter, and starting at 120 minutes, blood samples were taken immediately before each increase in flow rate, and then immediately before termination of the experiment at 145 minutes.

Figure 4A:
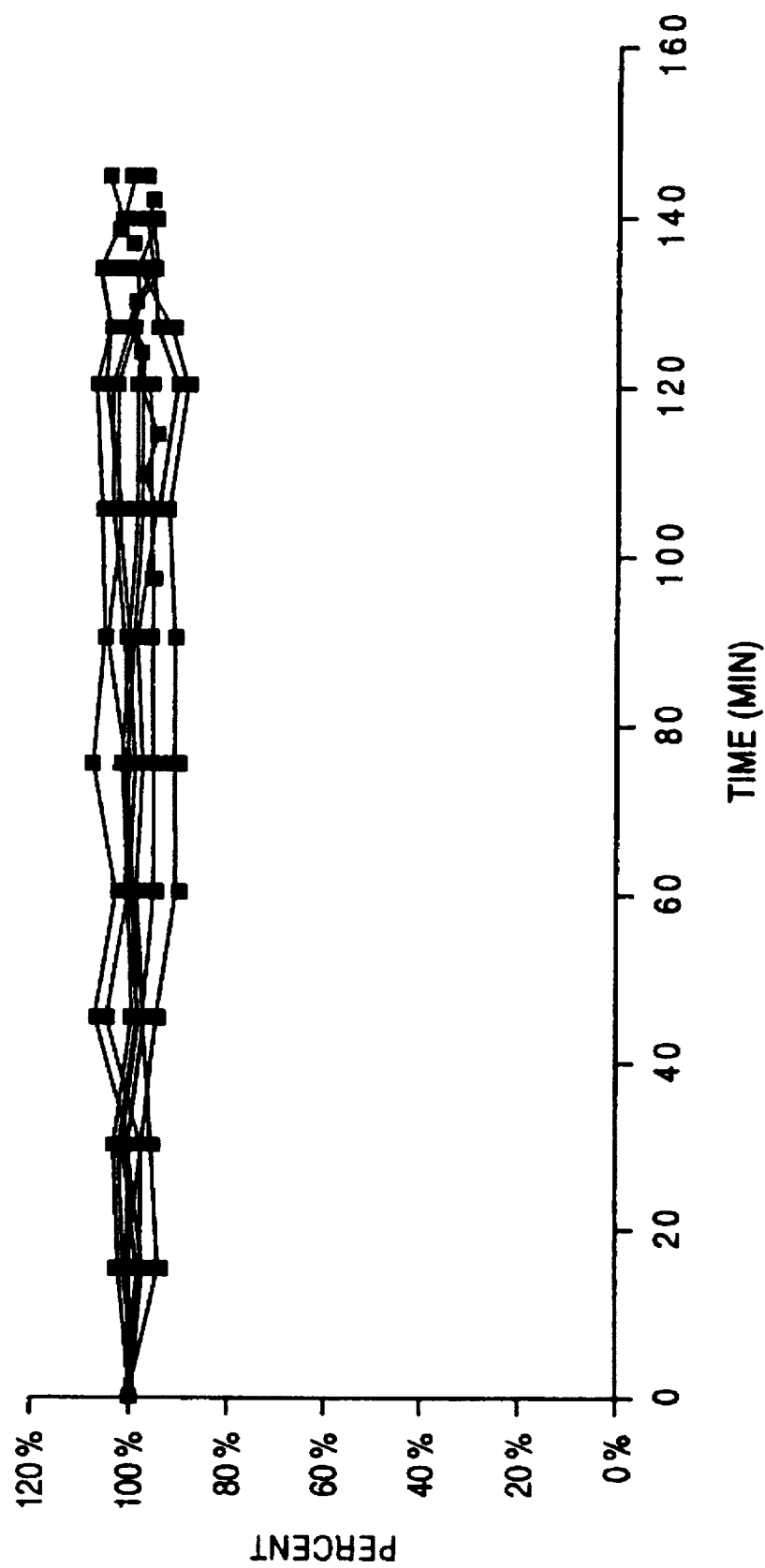
FIGS. 4A, 4B, 4C and 4D are graphs showing, respectively, white blood cell, red blood cell and platelet recovery.
Figure 4B:
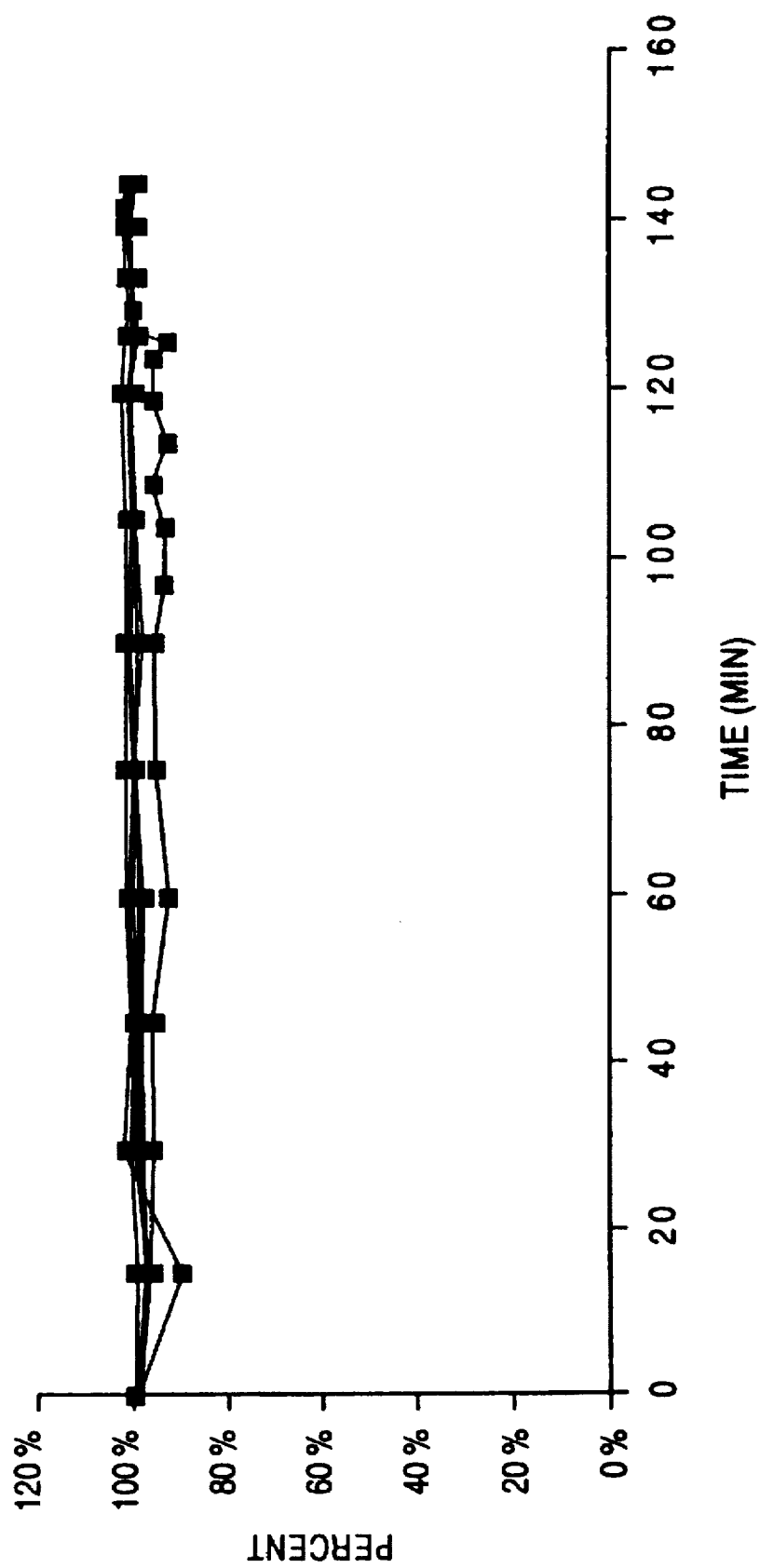
Figure 4C:
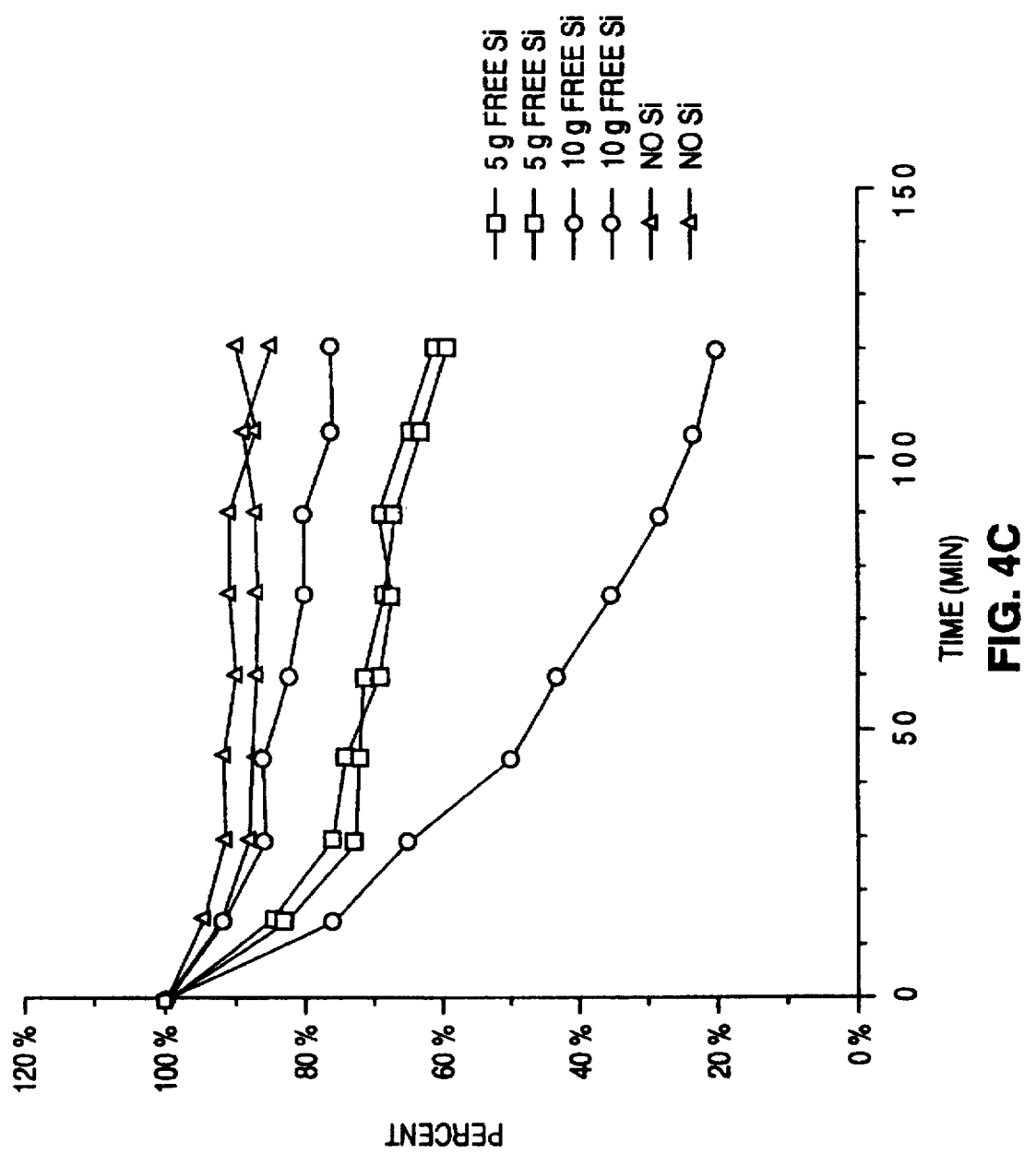

As is shown in FIG. 4A, the white blood cell recovery (corrected for dilution) was maintained at near 100% throughout the duration of the test. Similarly, as is shown in FIG. 4B, the red blood cell recovery (corrected for dilution) was maintained at 100% throughout the duration of the test. However, as shown in FIG. 4C, the platelet recovery (corrected for dilution) was not as consistent. A device without silica allowed 90% of the platelets to be recovered, however the devices containing silica caused significant loss of platelets. Therefore, based on the results from this test, it was clear that additional work was needed to ameliorate the problem of platelet loss.

Figure 4D:
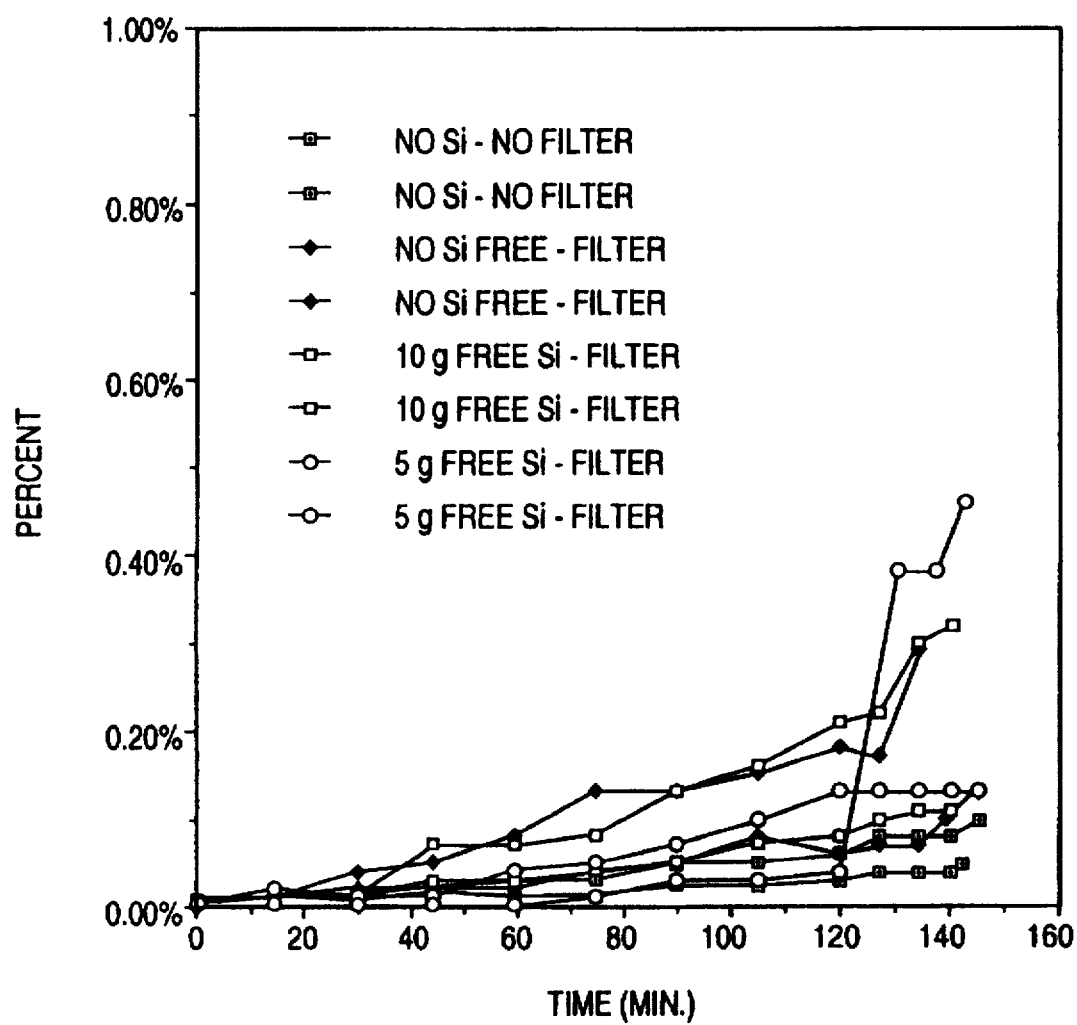

FIG. 4D shows that a constant flow rate of 50 ml/min for 120 minutes that the amount of hemolysis in a saline flushed column is maintained well below the 1% level, a level meeting, e.g., the current U.S. FDA standard for blood transfusion. Thus, this column does not cause significant hemolysis. Additionally, the 50 ml/min flow rate is equivalent to flow rates of 400–500 ml/min in a larger column, a column such as would be suitable for use for adult human treatment.

Example 4

Figure 5A:
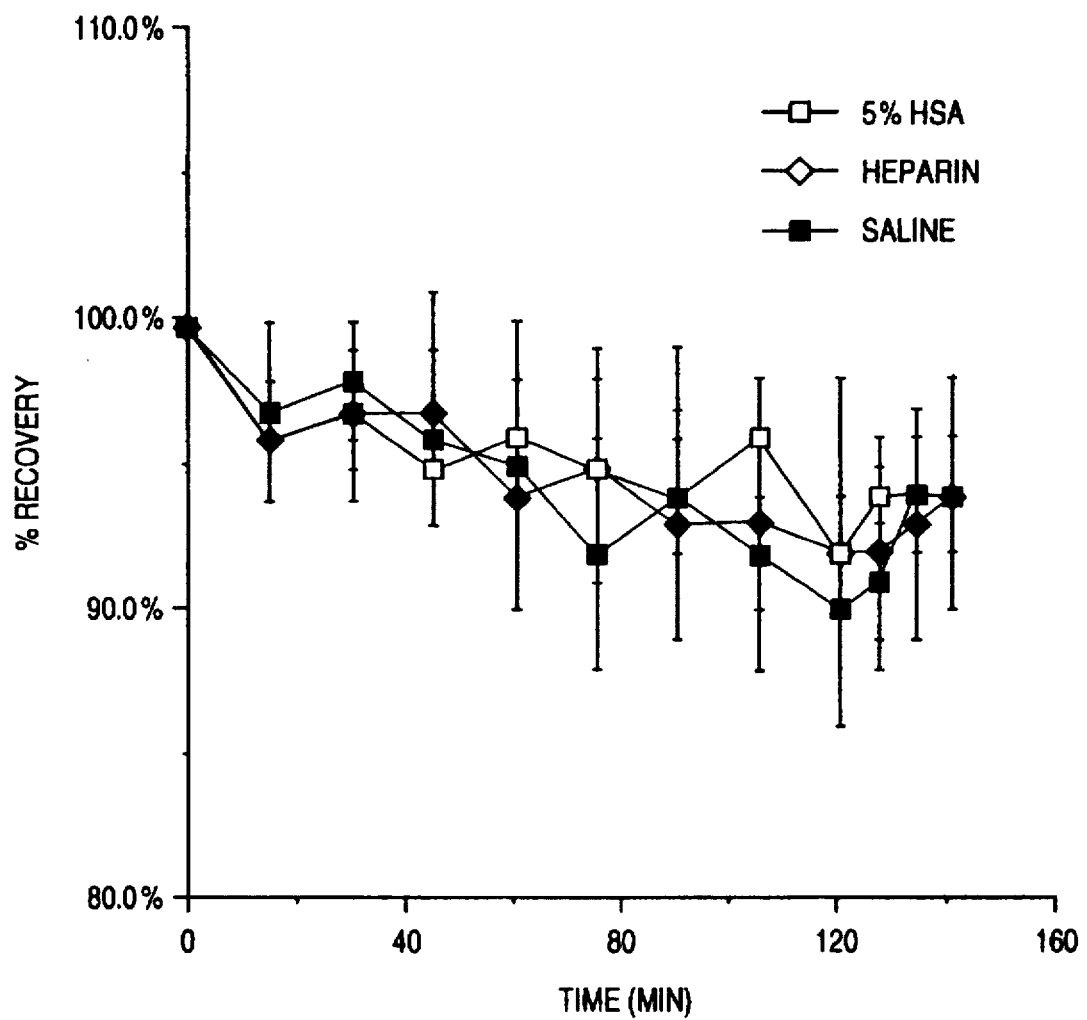
FIGS. 5A, 5B and 5C are graphs showing the recovery of white blood cells, red blood cells, and platelets, respectively, from citrated blood, using a number of different surface-treating candidates.
Figure 5B:
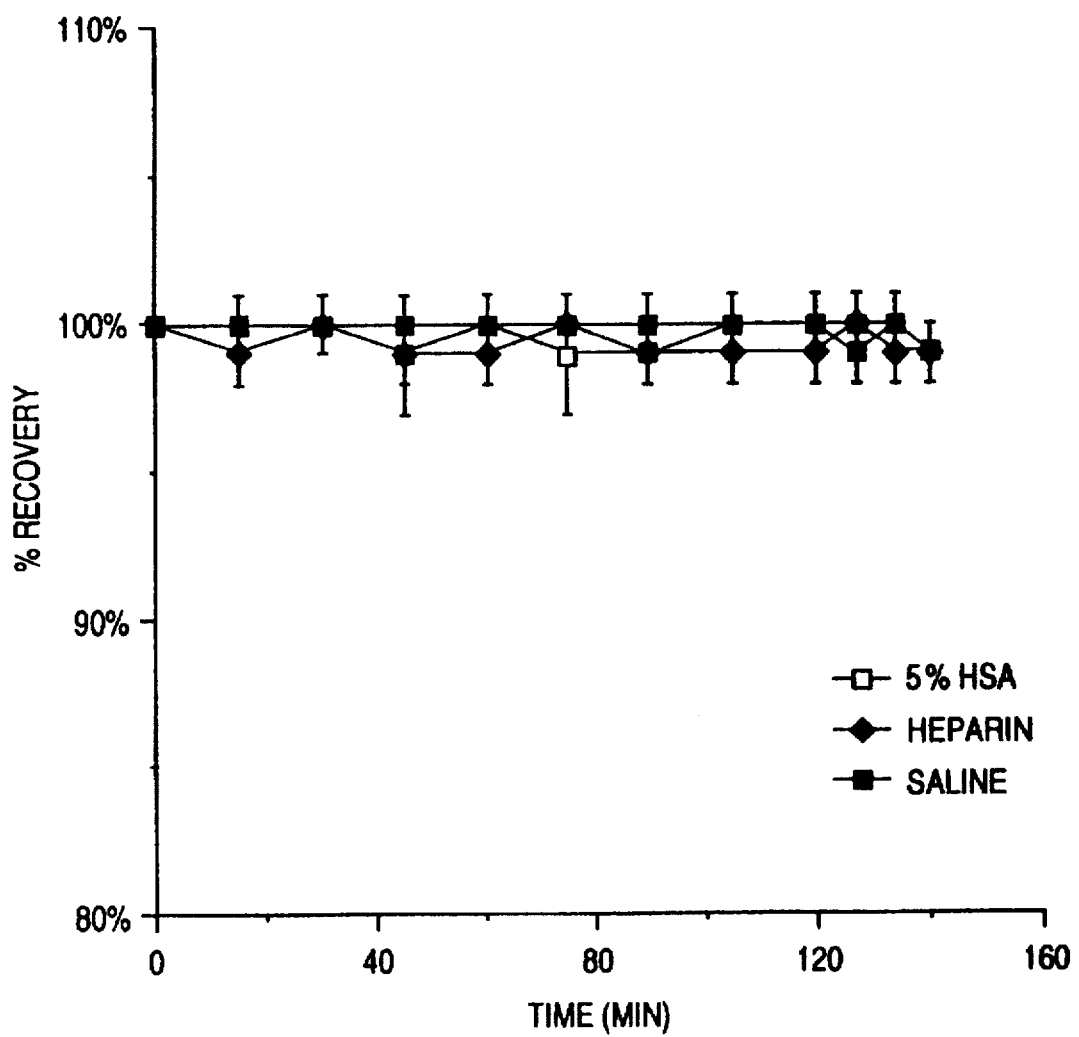
Figure 5C:
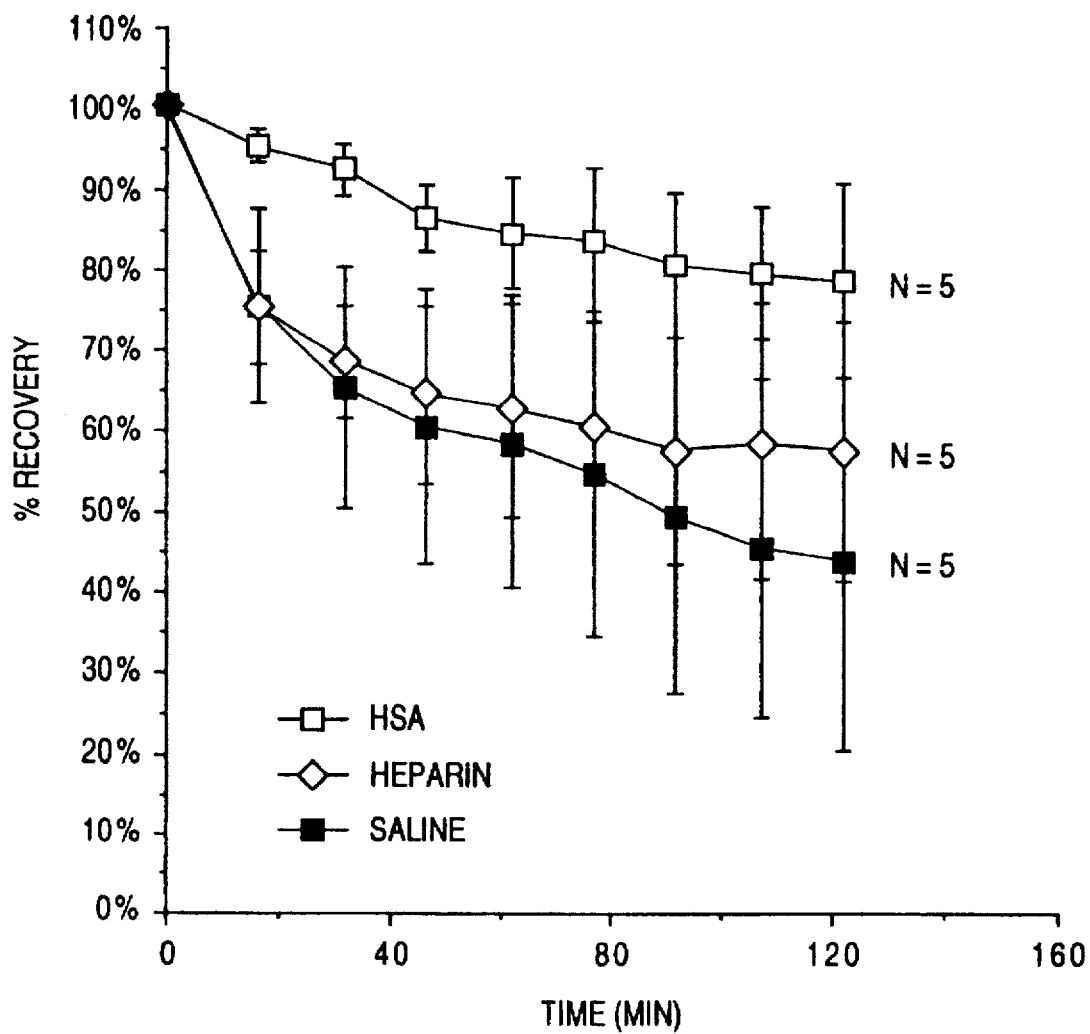

This example examines two different silica pretreating agents, to evaluate the extent of platelet and cell loss during treatment. The results from this experiment were evaluated to determine a preferred manner of treating silica to prevent undesired removal of cells from blood. The pretreating materials tested were a 5% solution of human serum albumin (HSA), and 10 U/ml of heparin in saline. A saline solution was used as a control. Data for this study are illustrated in FIGS. 5A–5C. For this example, test conditions corresponding to those described in Example 3 were employed.

As is shown in FIG. 5A, white blood cell recovery (corrected for dilution) for columns pretreated with either priming system corresponded with the unprimed, saline-flushed control columns. FIG. 5B shows that nearly 100% of the red blood cells (corrected for dilution) were recovered for each of the priming systems. FIG. 5C demonstrates that the HSA-treated silica had significantly higher platelet recovery (corrected for dilution) than either the heparin composition or the saline solution. On this basis, HSA is a preferred pretreating agent.

Figure 5D:
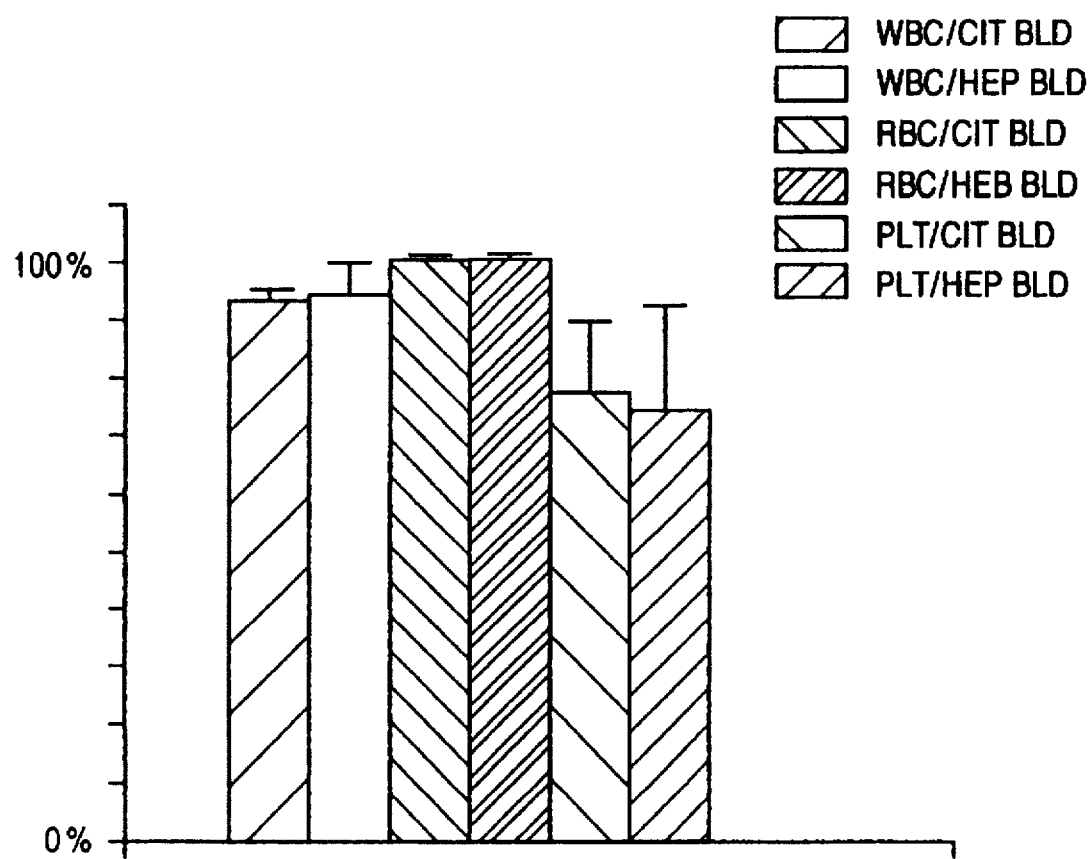
FIG. 5D compares heparinized and citrated blood, utilizing columns pretreated with HSA.

FIG. 5D compares citrated and heparinized blood when applied to HSA-treated columns. The similarity of the results for each type of anticoagulated blood indicates that either anticoagulation method can be used.

Example 5

This example evaluates the amount of hemolysis which occurred, as a function of the silica pretreating agent placed with the silica particles. The results from this experiment were evaluated to determine a preferred manner of treating silica to avoid undesired hemolysis. Once again, test conditions similar to those addressed in Examples 3 and 4 were employed.

Figure 6A:
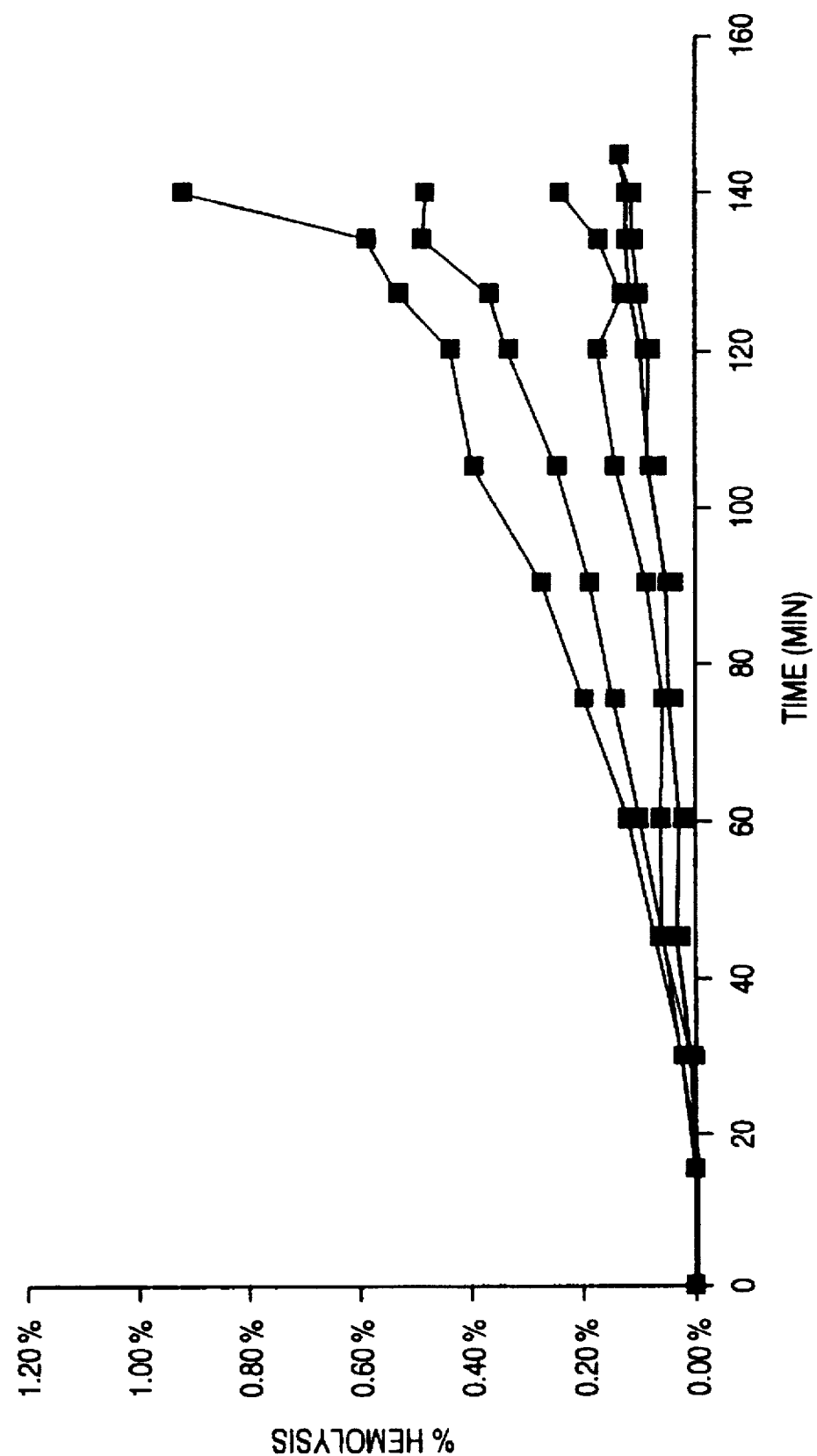
FIGS. 6A, 6B, and 6C are graphs depicting the hemolysis of citrated whole blood using saline (control), heparin silica pretreatment, and HSA silica pretreatment, respectively.
Figure 6B:
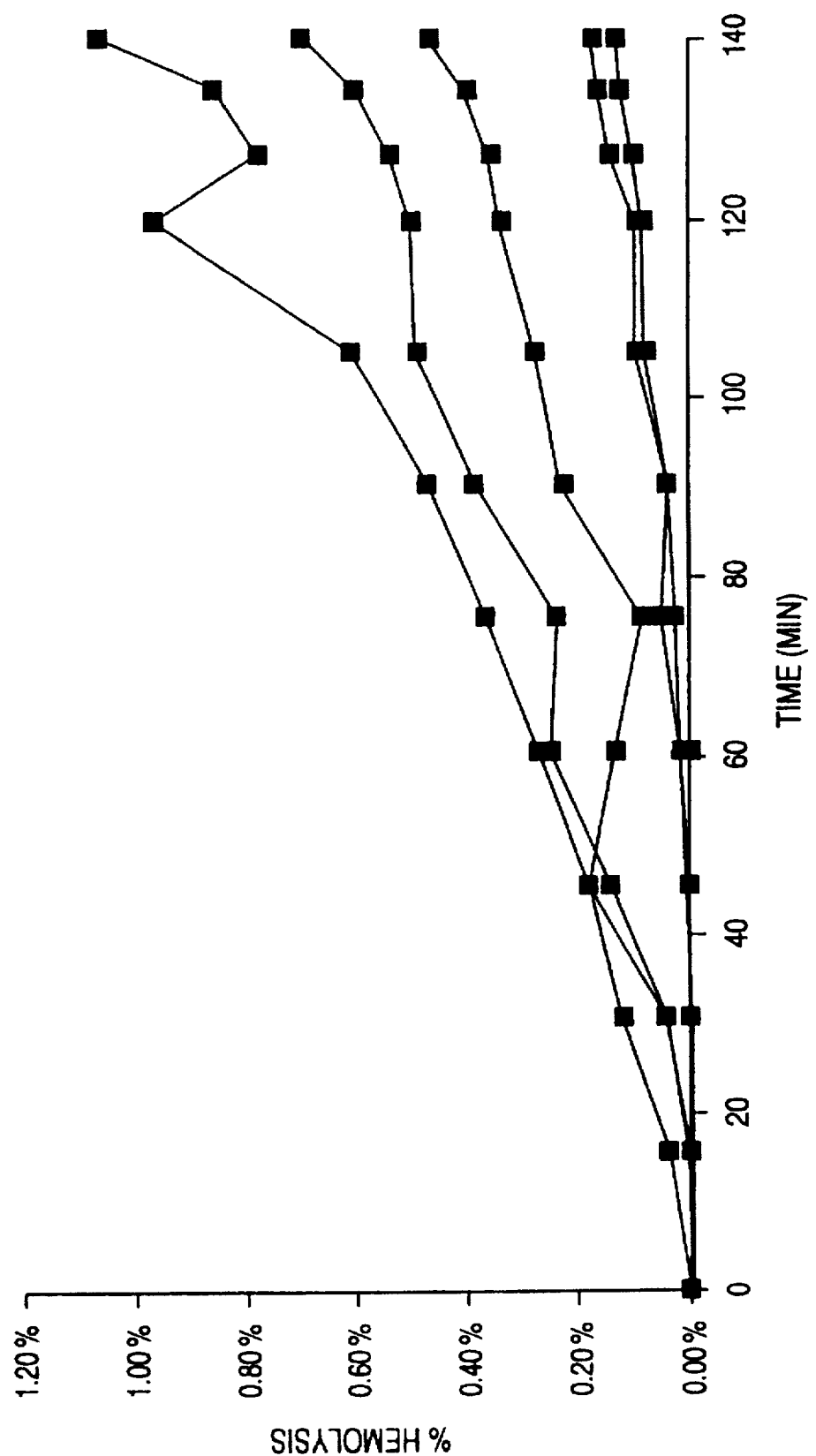
Figure 6C:
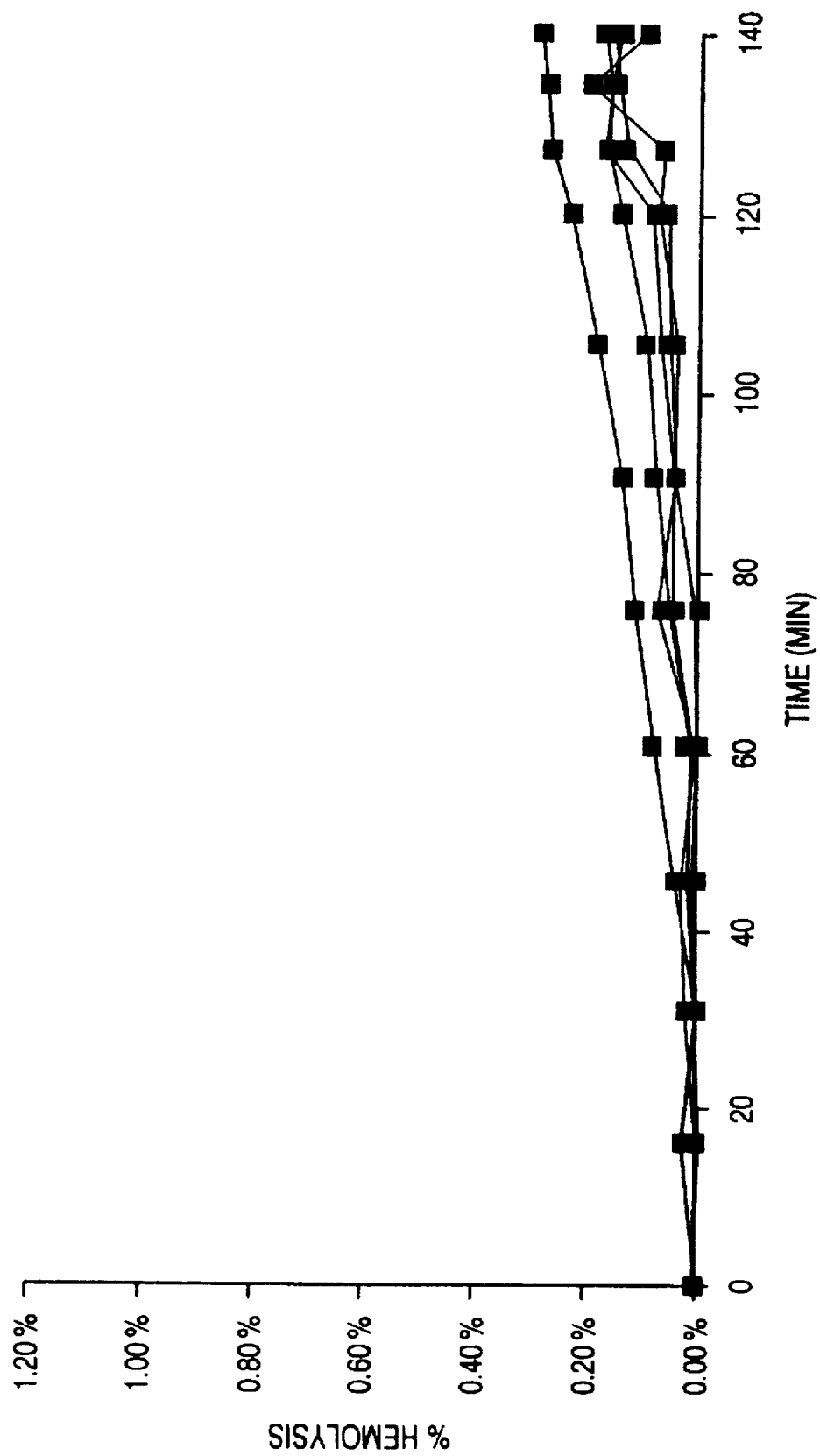
Figure 6D:
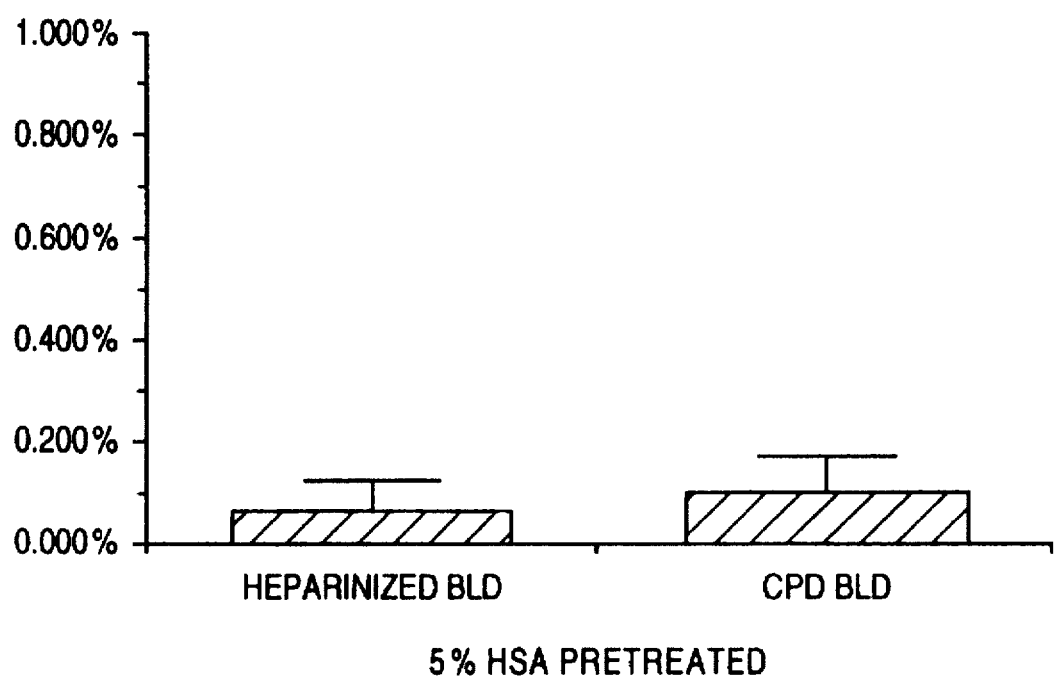
FIG. 6D compares hemolysis between citrated and heparinized blood when applied to columns pretreated with HSA.

FIG. 6A depicts results based on priming the column with saline solution. FIG. 6A shows that significant hemolysis approaching 1% begins to occur during the latter portion of the test, portions of the test during which flow rates were increased. Similarly, FIG. 6B shows that, with a heparin prime, the hemolysis reaches nearly 1% at 120 minutes. However, the silica primed with 5% HSA clearly prevented substantial hemolysis during the period of the test, as depicted in FIG. 6C. Accordingly, 5% HSA is a preferred silica pretreating agent.

Example 6

In this example, animal feasibility studies were performed using two subject populations: healthy young pigs (50–60 kg in weight); and juvenile pigs, both healthy and septic, (2–10 kg in weight). Cytosorb™I-A devices (an adult human device) were used to evaluate the young pigs (50–60 kg in weight). Cytosorb™III-A devices (a dimensionally similar small-scale device) were used to evaluate the juvenile pigs (2–10 kg in weight). Each of these Cytosor™ devices were produced in accordance with the present invention, and are available from Applied Immune Sciences, Inc., Santa Clara, Calif. Since the devices were dimensionally similar, the physical parameters relating to flow stress are similar, and thus safety data are comparable for the devices.

The septic juvenile pigs were produced according to a known sepsis model. The sepsis model was developed by A. Lee and J. Matson (Lee, A., et al., "Hemofiltration Removes Toxic Mediators and Prolongs Survival in *Staphylococcus aureus* Sepsis Acute Lung Injury", abstract provided at the 1990 World Conference on Lung Health; Lee, A., et al., "Continuous Arteriovenous Hemofiltration Therapy for *Staphylococcus aureus*-induced Septicemia in Immature Swine", *Critical Care Medicine*, in press) In this model, the sepsis was induced by intravenous injection of a lethal dose of *Staphylococcus aureus* over a one-hour period into an anesthetized pig. Use of this model is known to lead to death ($LD_{100}$) of a subject pig within approximately 24 hours.

After each septic juvenile subject was treated with a device in accordance with the invention for a period of six hours, the subject was then monitored closely for another three hours. The animals recovered from anesthesia and were returned to a separate pen for observation for seven days, or until death. Surviving animals were sacrificed at the end of the seven day period. A limited autopsy was performed on each subject at the time of death and tissues were taken for histological examination. The safety of the device was evaluated by careful measurement of physiological, laboratory and histological parameters. The physical performance of the device was assessed by pressure measurements, a sensitive indicator of resistance to flow resulting from changes in flow rate, clotting of blood or kinks in the flow path.

Figure 7:
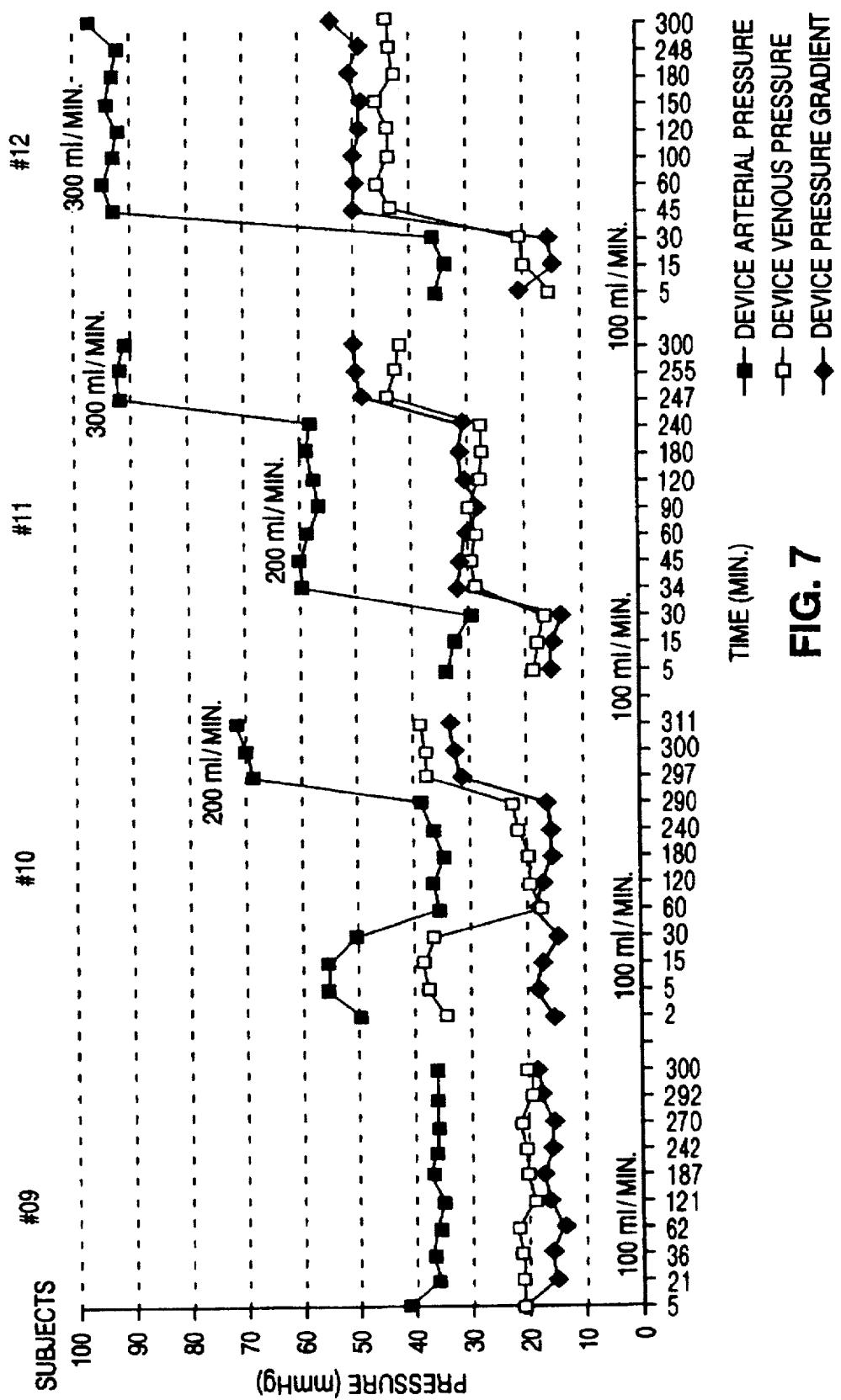
FIG. 7 is a detailed graph of the pressure versus time and flow behavior of normal young pig subjects #09–#12, wherein only citrate was used for anticoagulation.
Figure 8A:
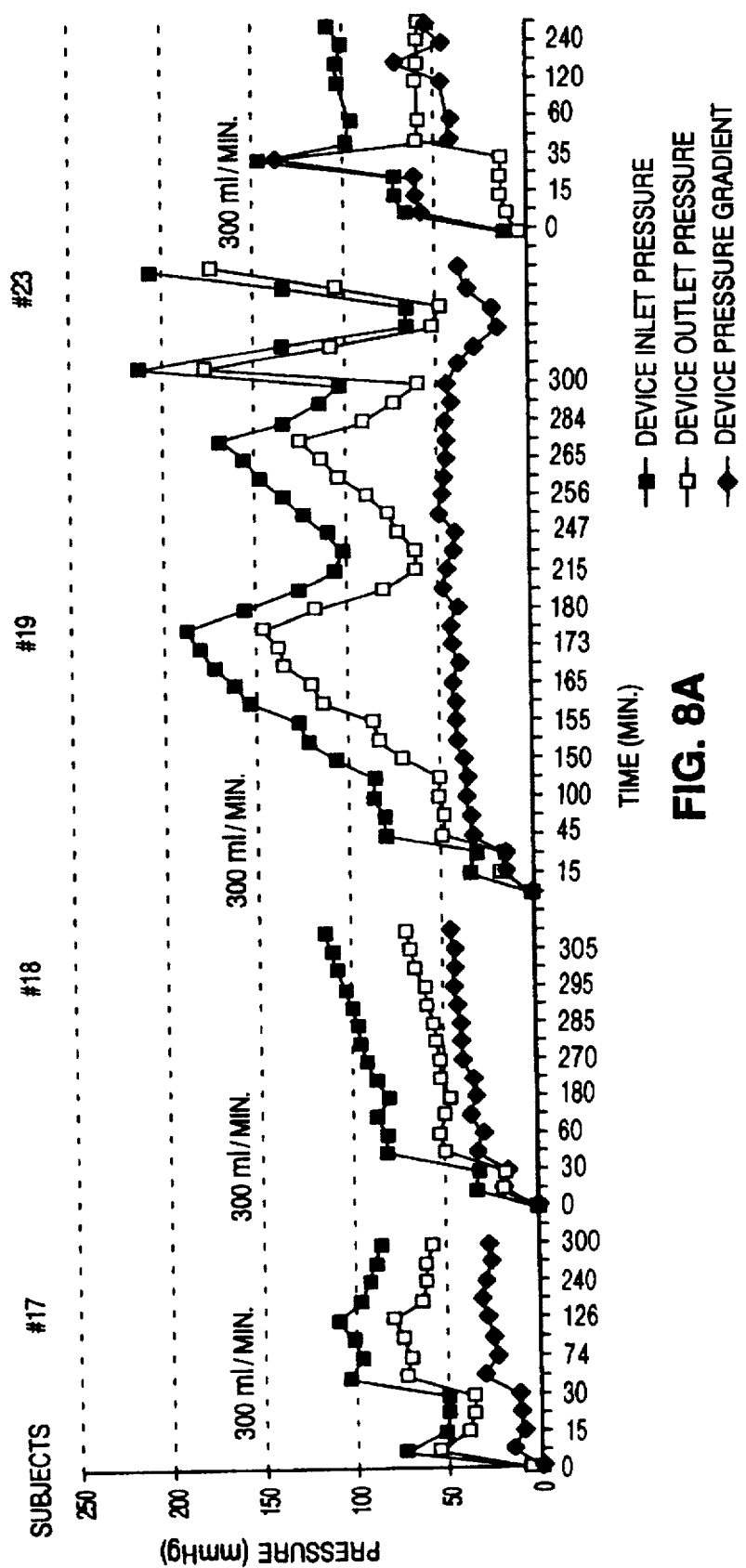
FIG. 8A depicts the pressure-versus-time profiles for normal young pig subjects #17–#19, and #23; these subjects underwent five hours of treatment using a combination of citrate and heparin for anticoagulation. In these experiments the amount of each anticoagulant was varied in order to determine the appropriate combination that allowed free flow with the minimal amount of each anticoagulant.
Figure 8B:
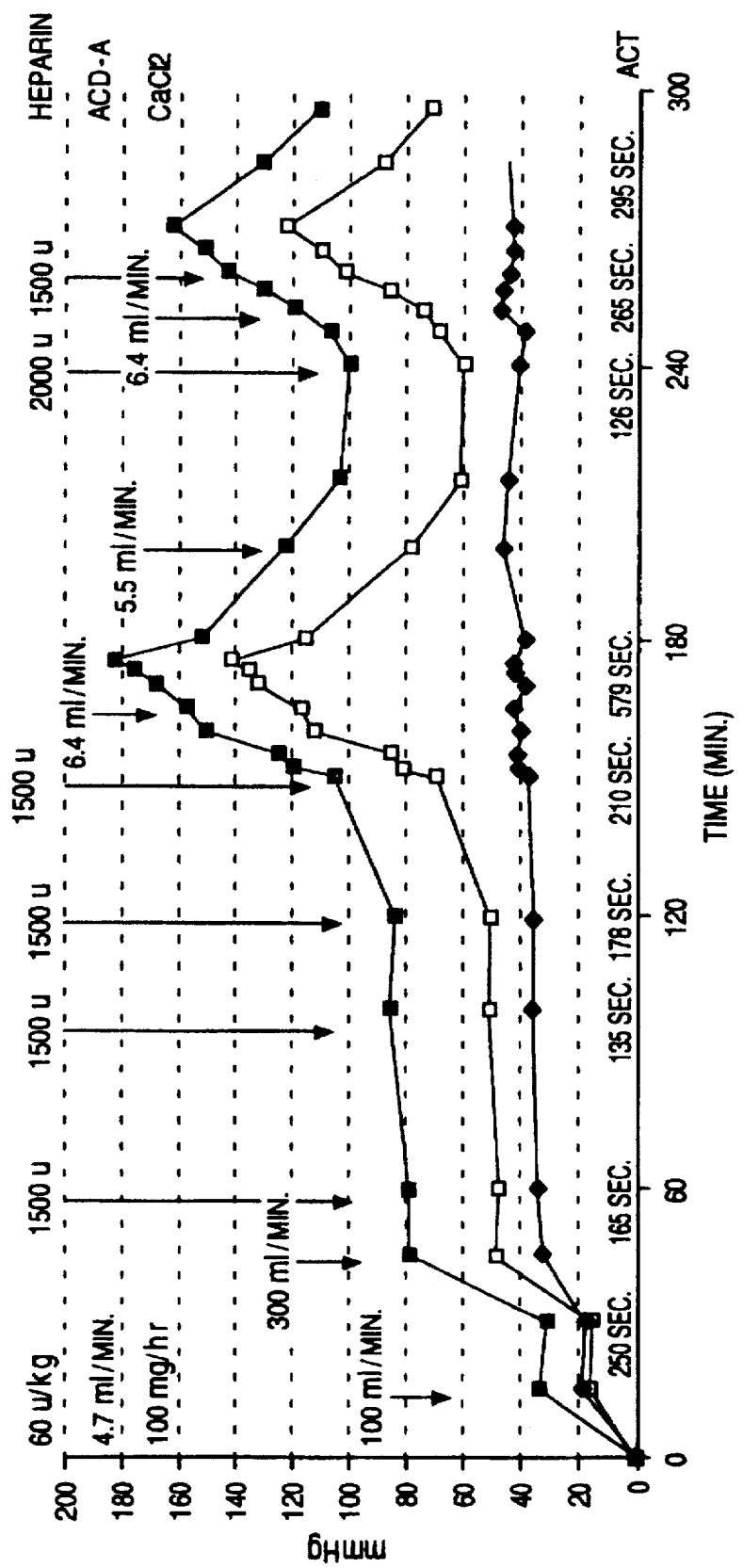
FIG. 8B corresponds to FIG. 8A, yet depicts the pressure-versus-time profile for normal young pig subject #19, in greater detail.

FIGS. 7, 8A, and 8B depict pressure-versus-time and flow (pressure-flow-time) data. In the studies which formed the basis for these figures, a subject's blood viscosity caused variation in the range of acceptable starting pressures. However, of greater concern than the absolute value of the starting pressure, was any increase from the baseline pressure, increases in device pressure were indicative of blockage of the device or an interference in flow.

Initial evaluations of blood processing in young healthy pigs with the Cytosorb™I-A device with heparin anticoagulation were not successful (data not shown). Most procedures ended early because of clot formation in the device. Accordingly, heparin alone was not an adequate anticoagulant.

The first anticoagulant regimen which allowed a full five hours of blood processing in young healthy pigs was accomplished using Acid Citrate Dextrose, NIH Formula A (ACDA), a citrate anticoagulant, at 7 milliliters (ml) per minute for blood flow rates up to 300 ml per minute (corresponding to a blood:anticoagulant ratio of approximately 45:1). The flow, pressure and time relationship of these successful studies are shown in FIG. 7 for normal young pig subjects #09–#12. The pressures were very stable and only changed with alterations in flow rates, behaving in a direct linear fashion based on each flow rate. These experiments established that procedures could be performed with citrate alone.

Pressure-flow-time data for normal young pig subjects #09–#12, wherein only acid citrate dextrose, NIH Formula A (ACDA) was used for anticoagulation, are depicted in FIG. 7. As shown, the pressures were very stable and behaved in a direct linear fashion based on each flow rate. This experiment establishes that procedures can be performed using citrate without any additional anticoagulant such as heparin. Although anticoagulation was achieved with citrate alone, the citrate infusion rate was high. The citrate regimen might not be well tolerated by smaller individuals. Due to the citrate levels employed, and a potential issue of citrate toxicity, it was desired to pursue a regimen that utilized lower anticoagulant amounts. Thus, regimens utilizing combined citrate and heparin were studied.

Additional studies were performed with different combinations of citrate (ACDA at 3–6 ml per minute) and heparin loading dose (60–150 units per kilogram) for blood flow rates of up to 300 ml per minute, to identify an alternative anticoagulant regimen using less citrate.

FIG. 8A depicts the pressure-time-flow profiles for normal young pig subjects #17–#19, and #23. Each of these experiments employed some combination of citrate and heparin. Accordingly, each subject had a different loading dose, thereafter heparin and citrate solutions were infused. The amount of each anticoagulant infused over time was varied, in order to determine a combination that provided for free flow while employing a minimal amount of each anticoagulant. Thus, the data derived from these subjects were of use in determining a preferred combination of citrate and heparin anticoagulant regimen. If clotting occurred, thereby producing a rise in pressure, more heparin, citrate, or both were given to stop the clotting process. Thereafter, the subject's own thrombolytic systems produced thrombolysis of the clot.

In the experiment on normal young pig subject #17, the subject was given a rather large loading dose of heparin, 150 units per kilogram of body weight, and the ACDA was reduced to 3 ml per minute starting at 90 minutes with a blood flow rate of 300 ml per minute. After about 30 minutes, the pressure rose (FIG. 8A), indicating clotting in the device. The ACDA infusion rate was increased to 4.7 ml per minute and the procedure was carried to completion. Additional heparin was not needed to stop the clotting process, suggesting that the 150 unit per kilogram loading dose was perhaps more than needed.

In the experiment on normal young pig subject #18, the initial heparin loading dose was reduced to 100 units of heparin per kilogram of body weight; the ACDA infusion rate was 4.7 ml per minute (corresponding to a blood:anticoagulant ratio of approximately 60:1). The activated clotting time (ACT) of the blood was checked periodically; 30 units of heparin per kilogram was given if the ACT was near or below 200 seconds. The pressures were very stable for the first 270 minutes. At 270 minutes, the ACDA infusion rate was reduced to 4.2 ml per minute. The pressure slowly rose over the next 30 minutes indicating clot formation in the system. These first two experiments indicated that ACDA flow rate of 4.7 ml per minute was probably the minimal amount necessary regardless of the amount of heparin given. This experiment showed that this combination of citrate and heparin was capable of maintaining adequate anticoagulation for the operation of the device.

The experiment on normal young pig subject #19 began with a loading dose of only 60 units of heparin per kilogram, and a flow rate of 4.7 ml per minute of ACDA. Thirty units of heparin were given when the ACT fell near or below 200 seconds. Additional heparin was required by 60 minutes, then in rapid succession at 100, 120, and 155 minutes. In spite of the heparin, the pressures continued to rise due to clotting in the device. ACDA flow rate was the flow rate was then increased to 6.4 ml per minute, but the pressure did not respond. Additional heparin was given at 260 minutes and the pressure slowly decreased with time. The pressure time profile of this procedure is displayed in greater detail in FIG. 8B. The experience with this procedure indicated that the 60 units of heparin per kilogram loading dose was not adequate and the 30 units per kilogram of heparin as a bolus injection was just marginal; and that the resulting clotting was reversible with a combination of increased doses of heparin and ACDA.

Based on the previous three experiments (with normal young pig subjects 17, 18 and 19), a heparin loading dose of 100 units per kilogram of body weight and a low rate of 4.7 ml per minute of ACDA was determined to provide the best anticoagulation results, as shown in experiment on subject #18. The experiment on subject #23 was a repeat of the procedure on subject #18. The procedure was completed without significant problems. This combination of citrate and heparin allowed for a reduction in ACDA by one-third, compared to the citrateonly study depicted in FIG. 7.

The experiments on healthy young pig subject #19 did not set forth the preferred anticoagulation regimen, since clotting did occur with this level of anticoagulation. However, since clotting did occur, this provided a scenario wherein the modulation of clotting could be evaluated. The modulation of clotting in the experiments with subject #19 is illustrated in FIG. 8A, as shown by the saw-tooth pattern of the profile for subject #19. The pressure-versus-time profile of young pig subject #19 is shown in greater detail in FIG. 8B.

Accordingly, FIG. 8B depicts further studies wherein young pig subject #19 was given both heparin and ACDA. In one aspect, the loading dose given to subject #19 was not preferred in that clotting did result. In another aspect, however, the fact that clotting did occur allowed for study of the ability to modulate clotting. Referring to FIG. 8B, and beginning at about 150 minutes into the study, increasing doses of heparin did not lead to a decrease in the pressure within the device. However, upon addition of ACDA to the heparin, and allowing for a lag time before it took effect, the ACDA yielded a pressure drop. Beginning at about 250 minutes into the study, the device pressure again began to rise. During this second pressure rise, initially citrate alone was given. This infusion of citrate did not seem to lead to diminution of pressure. Upon addition of heparin, however, a pressure decrease did occur. Thus, the data represented in FIG. 8B indicates that a combination of citrate and heparin is particularly advantageous for use in modulating clotting within a device.

Example 7

Figure 9:
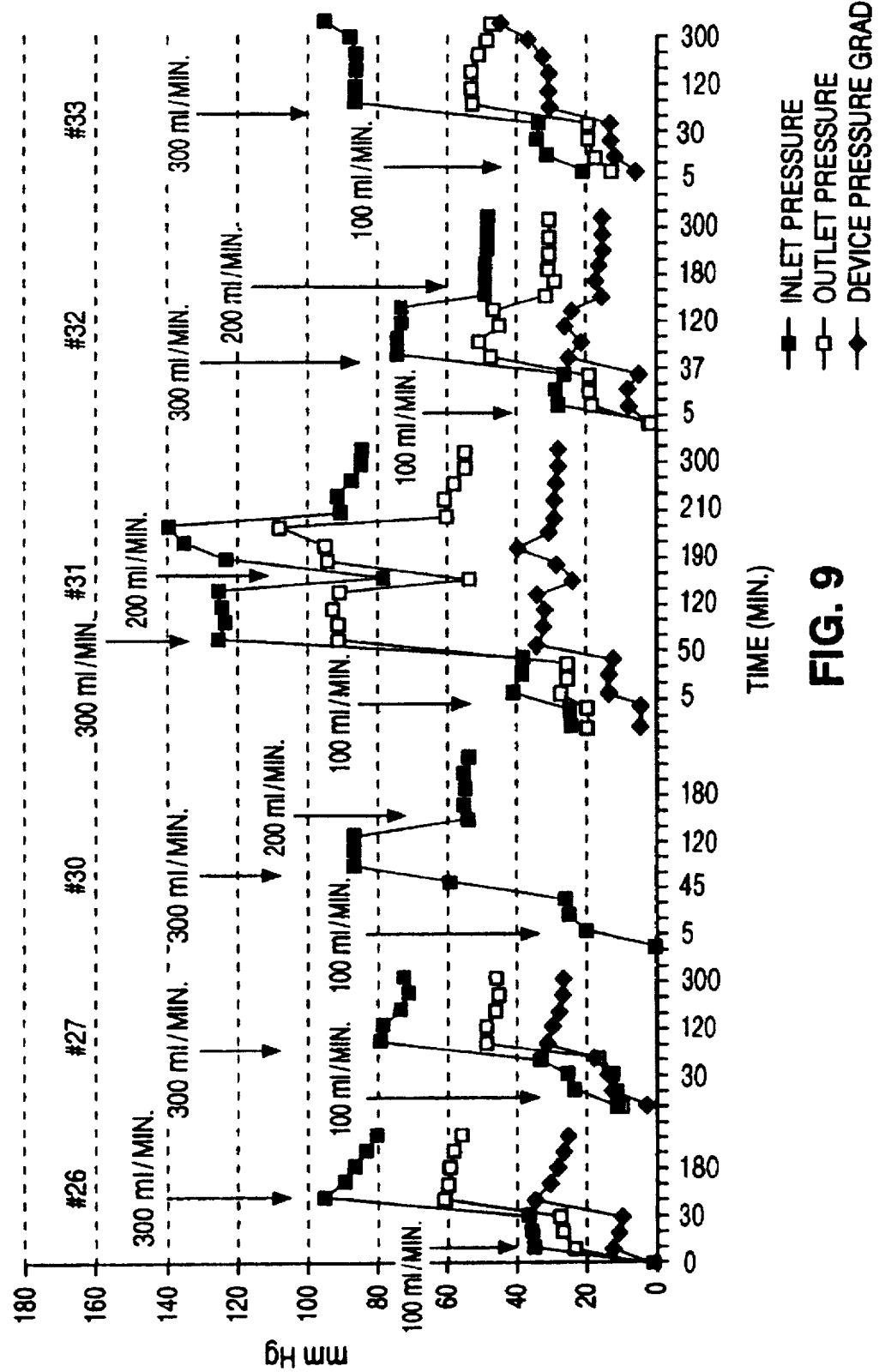
FIG. 9 shows the pressure-flow-time profiles for the six normal young pig subjects which had undergone a five-hour hemoperfusion procedure with a device in accordance with the present invention. All procedures used a combination of citrate and heparin for anticoagulation.
Figure 10:
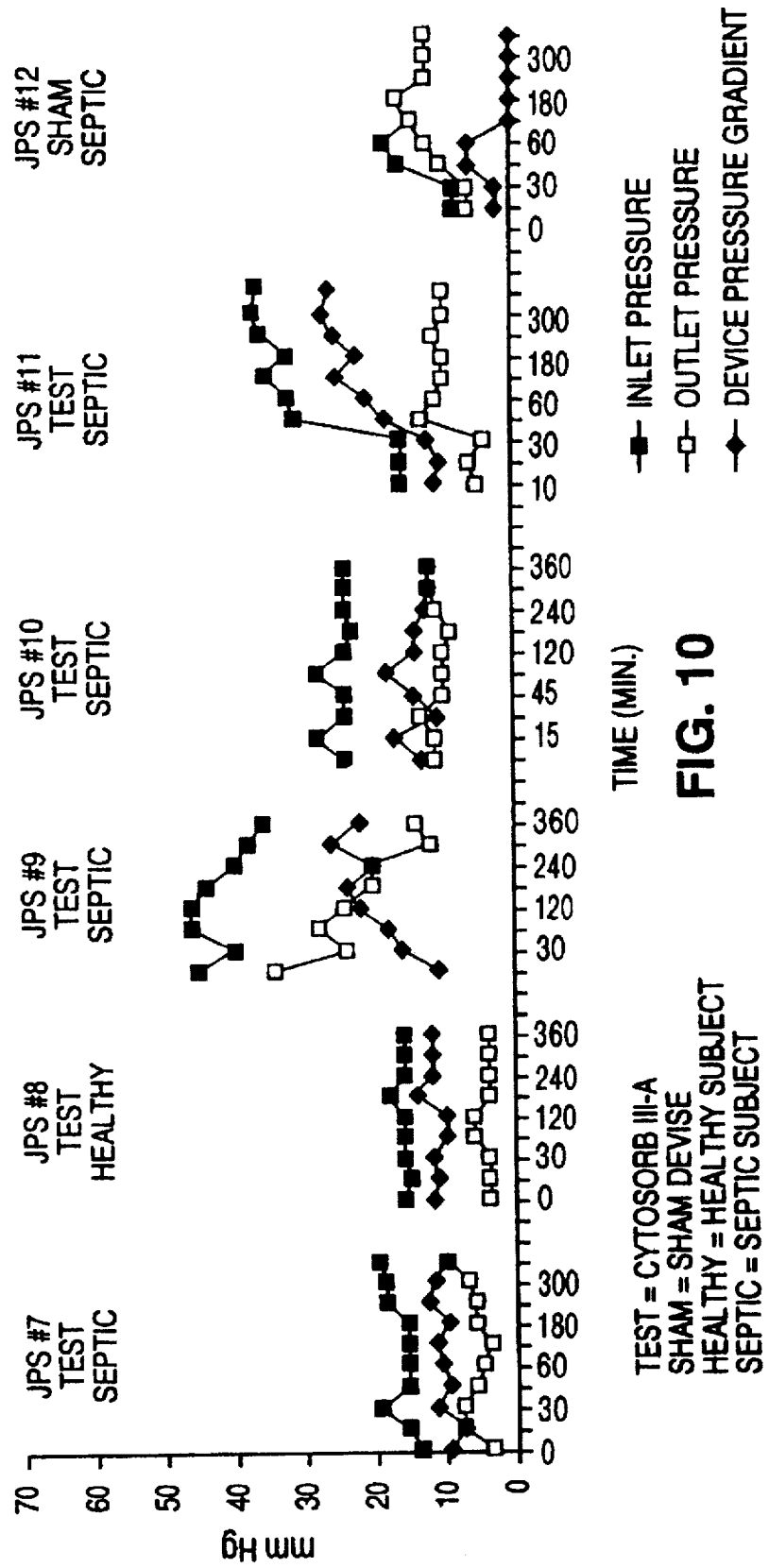
FIG. 10 shows the pressure-time profiles of healthy and septic subjects which had successfully undergone six hours of blood processing with a device in accordance with the invention, using a combined citrate and heparin anticoagulation regimen.

The preferred combined citrate and heparin anticoagulant regimen was further tested in healthy young pigs, and in healthy and septic juvenile pigs. The pressure-time profiles for these experiments in healthy young pigs (#26, #27, #30–#33) using the Cytosorb™I-A device are shown in FIG. 9. The pressure-time profiles for these experiments in healthy and septic juvenile pigs using the Cytosorb™III-A device, along with control data from use of a sham device, are shown in FIG. 10. These experiments were performed with a heparin loading dose of 100 units per kilogram of body weight and 4.7 ml per minute of ACDA for young healthy pigs, or 100 units of heparin per kilogram of body weight and 0.33–1.0 mg of citrate per ml of blood (equivalent to 4.7 ml of ACDA per minute) for the juvenile pigs. The blood flow rates were between 100 and 300 ml per minute for the young healthy pigs, and between 30 and 80 ml per minute for the juvenile pigs. If the activated clotting time (ACT) fell to a level near or below 200 seconds, additional heparin was given. Heparin was given either in a bolus injection of 30 to 40 units per kilogram of body weight or as a continuous infusion of 30–40 units of heparin per kilogram per hour. All of these experiments showed stable pressures for any given flow rate, and the subjects tolerated the procedures well, as discussed below. These experiments were successfully carried out for five to six hours of blood processing.

FIGS. 9 and 10 illustrate the pressure-flow-time profiles of healthy and septic subjects which successfully underwent five to six hours of blood processing in accordance the invention, while using a combined citrate and heparin anticoagulation regimen. In the studies upon which these figures are based, the variation among individual subject's blood viscosity produced variation in what an acceptable starting pressure was. Any increase from the baseline pressure was of greater concern than the absolute value of the starting pressure. Increases in device pressure tend to indicate blockage of the device or an interference in flow.

FIG. 9 illustrates the pressure-flow-time profiles for the six normal young pigs which underwent a five-hour hemoperfusion procedure with the Cytosorb™I-A device. For these studies, the uniform loading dose of 100 U heparin/kg; an initial ACDA flow rate of 4.75 ml/min; a continuous infusion of heparin of 40 U heparin/kg/hr; and an initial blood flow rate of 100 ml/hr were employed. All procedures were carried to completion using a combination of citrate and heparin for anticoagulation. Increases in device pressures were due to increases in flow rate or obstructions to flow such as clots. The stability of the pressure-flow-time lines (taking into account pressure changes based on changes in flow) indicates that the device continued to function and that neither clotting nor obstruction prevented use of the device. For example, subject #33 in FIG. 9 showed an increase in device pressure based on a clot within the device, since inlet pressure rose whereas the outlet pressure was stable and actually began to decrease. The clotting within the device for subject #33 was readily controlled by the anticoagulation regimen. Subject #31 experienced a clot at a time between 120 and 190 minutes. The pressure changes resulting from this clot are suggestive of a clot distal to the device, due to increases in both inlet and outlet pressures. Clotting during the experiment on subject #31 was also readily controlled by the anticoagulation regimen.

FIG. 10 illustrates the pressure-flow-time profiles for the six juvenile pigs which underwent a six-hour hemoperfusion procedure with the Cytosorb™III-A device. For the procedures represented in FIG. 10, the uniform loading dose of 100 U heparin/kg; a trisodium citrate concentrate in sufficient quantity to provide 0.33 mg of citrate per ml of whole blood; a continuous infusion of heparin at 40 U heparin/kg/ hr; and blood flow rate between 30–60 ml/min, were all employed. As shown in FIG. 10, juvenile pig subject #11 experienced a pressure change due to a clot within the device. However, this clotting was readily controlled by the anticoagulation regimen.

The results shown in FIGS. 9 and 10 illustrate that blood from both septic and healthy subjects can effectively utilized within devices in accordance with the invention.

To summarize, our experiments showed that free flow through the device can be maintained with the following anticoagulant regimens:

I. Acid Citrate Dextrose, NIH Formula A (ACDA), at ratios of blood to anticoagulant (V/V) of 45/1 or less for whole blood flow rates of 300 ml/min or less.

II. A combination of citrate anticoagulant and heparin:
  A. Acid citrate dextrose, NIH Formula A (ACDA) at ratios of blood of anticoagulant (V/V) of 60/1 or less for whole blood flow rates of 300 ml/min or less; together with heparin (100 U/kg), given at the onset of the procedure, and heparin given in sufficient quantities as bolus injections or continuous infusion to maintain an activated clotting time of more than 200 seconds.
  B. Trisodium citrate concentrate in sufficient quantity to provide at least 0.33 mg of citrate per ml of whole blood (equivalent to 0.5–1.5 mg citrate/ml of blood), for flow rates of 300 ml/min or less; together with heparin (100 U/kg) given at the onset of the procedure, and heparin given in sufficient quantities as bolus injections or continuous infusion to maintain an activated clotting time of more than 200 seconds.

Example 8

The laboratory and physiological results of two controlled studies under the regulations of Good Laboratory Practices are shown in Tables 2–5 for the juvenile pigs, and in Tables 6–8 for the young healthy pigs. These pigs were obtained and treated according to procedures set forth in Examples 6 and 7. The hematological values for the healthy young pigs and juvenile pigs all showed a time-dependent decrease in white blood cells, red blood cells, fibrinogen and platelet counts (Tables 2 and 6). The decreases were due to dilution from priming solution in the device and due to the administration of anticoagulants. These time-dependent changes, when compared to the respective control groups for the healthy young pigs and the septic juvenile pigs, did not produce any clinically significant difference. These results again indicated that the device was not causing any clinically significant loss of blood cells, particularly platelets.

The blood chemistry values for both study groups remained, for the most part, unchanged. A few values showed a slight increase, such as blood calcium, inorganic phosphorus, and serum glutamic oxaloacetic transaminase (SGOT). The increase in calcium was the resulted from the use of citrate, a calcium chelating agent, and the concomitant administration of calcium ion as a prophylaxis for hypocalcemia. The increase in inorganic phosphorus was most likely the indirect result of citrate binding of calcium, resulting in mobilization from bone by the action of parathyroid hormone. The increase in SGOT was very slight and not clinically significant.

Blood chemistry studies showed that the use of the device did not have any clinically significant effects on blood components or other tissues or organs. Additionally, when the test groups were compared to their respective control groups, no statistically significant differences were found (data not shown).

The studies of physiologic parameters Tables 3 and 7) showed that because citrate administration induced metabolic alkalosis, a known effect, the pH tended to increase and the blood base content increased as reflected by the base excess and increased bicarbonate. The healthy young pigs also showed slight increases in central venous pressure and pulmonary wedge pressure, due to the expanded blood volume resulting from the priming fluid and the administration of anticoagulant; however, these changes were small and were not clinically significant. Comparison between the test and control groups showed, as the only clinically significant value, that the respiratory rate was significantly higher in the septic juvenile pigs treated with the sham device (without silica) than in the septic juvenile pigs treated with the Cytosorb™III-A device. The higher respiratory rate is suggestive of respiratory distress, which was not seen while the subjects were treated with the device.

In summary, both the feasibility and subsequent control studies in animals indicated that the device can be used effectively to process blood for five to six hours without adverse effects on the blood. Clotting problems were successfully avoided using the selected anticoagulant regimens of citrate or a combination of citrate and heparin, without which free flow through the device would not be possible.

Example 9

IN VITRO ISOTHERM PHARMACEUTICAL ADSORPTION BY AMORPHOUS SILICA

When subjected to simulated hemoperfusion or plasma perfusion, silica is understood to adsorb pharmaceuticals such as amitriptyline, digoxin, digitoxin, methaqualone, phenobarbital and phenytoin. Thereafter, it is also understood that these pharmaceuticals can be eluted from the silica. However, silica has not been utilized to remove pharmaceuticals from whole blood or plasma, such as for use in treating drug overdosage. The silica composition in accordance with the invention removes pharmaceuticals from whole blood in a manner whereby the blood can be returned to its donor. The silica composition can also remove pharmaceuticals from plasma.

The drug adsorbance of silica (PQ10150 sodium silicate gel, PQ Corp., Valley Forge, Pa.) with a mean particle size of 230 μm and a surface area of 400 m²/g pretreated with human serum albumin or heparin is set forth herein.

Evaluations are made of pharmaceutical solutions of: 2 ml of plasma containing drugs at 4 different concentrations, or 2 ml of whole blood containing drugs at 4 different concentrations ((each being serial 50% dilutions of the initial concentrations). Pharmaceuticals such as gentamicin, procainamide, quinidine, insulin, lidocaine, amitriptyline, desipramine, digoxin, ethosuximide, cocaine, theophylline, phenobarbital, acetaminophen, phenytoin, ethylene glycol, methotrexate, salicylate, thiocyanate and diazepam were evaluated.

Thereafter, pharmaceutical-saline solutions are produced by adding the pharmaceutical solutions to 1 ml buffered saline (as controls), or by adding the pharmaceutical solutions to 1 ml of buffered saline containing 0.3 gm of silica composition in accordance with the invention. The pharmaceutical-saline solutions are agitated for 40 minutes at room temperature.

The resulting differences in drug concentration between silica-treated and control specimens are measured by HPLC (Spectraphysics) for tricyclics and benzodiazepines, fluorescence polarization assay for digoxin using a TDX analyzer (Abbott Labs,Abbott Part, IL), and EMIT assay (Syva, San Jose, Calif.) using Monarch 2000 analyzer (Instrumentation Laboratory) for all other drugs. Cocaine levels are measured by Nichols institute, San Diego, Calif., by quantitative radioimmunoassay. Insulin levels are measured by Associated Regional and University Pathologists (ARUP) inc., Salt Lake City, Utah, by radioimmunoassay.

The results of these studies show that 99% of gentamicin is adsorbed up to a drug concentration of 7 μg/ml, and 88% from concentrations up to 17 μg/ml. A mean of 83% procainamide (from a drug in the concentration range 6 to 36 μg/ml), and 84% N-acetyl procainamide (drug concentration range 2 to 40 μg/ml) is adsorbed when both are present in the pharmaceutical-saline solution. 89% quinidine is adsorbed at a low concentration (2 μg/ml), with adsorption of 75% at the highest concentration (17.75 μg/ml). 88% insulin is adsorbed at a concentration of 5687 uU/ml, which decreased to 65% at a concentration of 46640 uU/ml. 74% of lidocaine is removed (drug concentration range 12 to 100 μg/ml). 73% of amitriptyline is adsorbed for concentrations between 275 and 2100 ng/ml. 44% of desipramine is adsorbed for concentrations between 400 and 3000 ng/ml. 12% of total digoxin (2 to 23 μg/ml) and 14% of the free digoxin fraction is removed. There is 5% adsorption at a concentration of 80 μg/ml ethosuximide, ranging to 8% adsorption at an ethosuximide concentration of 950 μg/ml. There is no significant adsorption of cocaine, theophylline, phenobarbital, acetaminophen, phenytoin, ethylene glycol, methotrexate, salicylate, thiocyanate and diazepam.

Accordingly, it is found that significant amounts of charged, non-protein bound drugs are removed by the silica composition produced accordance with the invention.

TABLE 3

Juvenile Pig Summary Hematology Statistics Table

| Parameters | Time | N | Control Treated Mean | St Dev | N | Septic Treated Mean | St Dev | N | Septic Sham Mean | St Dev |
|---|---|---|---|---|---|---|---|---|---|---|
| Hematocrit (%) | 60 | 6 | 25.2 | 1.2 | 6 | 27.3 | 3.7 | 6 | 24.5 | 1.8 |
|  | 420 | 6 | 18.3 | 2.1 | 6 | 17.3 | 2.3 | 4 | 17.8 | 2.1 |
| Platelets | 60 | 6 | 180333 | 53440 | 6 | 202000 | 53710 | 6 | 190667 | 24337 |
| (cells/cu. mm.) | 420 | 6 | 129000 | 20474 | 6 | 113833 | 40921 | 4 | 118750 | 21960 |
| White Blood Cells | 60 | 6 | 13783 | 2982 | 6 | 14550 | 3755 | 6 | 15183 | 5747 |
| (cells/cu. mm.) | 420 | 6 | 11683 | 947 | 6 | 11133 | 3830 | 4 | 8025 | 1825 |

TABLE 4

Juvenile Pig Summary Chemistry Statistics Table

| Parameters | Time | N | Control Treated Mean | St Dev | N | Septic Treated Mean | St Dev | N | Septic Sham Mean | St Dev |
|---|---|---|---|---|---|---|---|---|---|---|
| Albumin (gm/L) | 60 | 6 | 3.30 | 0.35 | 6 | 3.30 | 0.30 | 6 | 3.30 | 0.30 |
|  | 420 | 6 | 3.30 | 0.29 | 6 | 3.30 | 0.21 | 5 | 3.40 | 0.26 |
| Alkaline Phosphatase | 60 | 6 | 190.00 | 27.10 | 6 | 186.30 | 21.44 | 6 | 165.50 | 16.90 |
| (units/L) | 420 | 6 | 157.50 | 22.92 | 6 | 144.50 | 13.44 | 5 | 134.40 | 12.86 |
| Amylase (units/L) | 60 | 6 | 2262.70 | 818.99 | 6 | 1697.00 | 612.44 | 6 | 1987.20 | 327.15 |
|  | 420 | 6 | 2120.00 | 623.33 | 6 | 1586.50 | 210.13 | 5 | 1697.40 | 349.79 |
| BUN (mg/dL) | 60 | 6 | 21.20 | 2.23 | 6 | 15.30 | 3.67 | 6 | 19.50 | 1.97 |
|  | 420 | 6 | 21.70 | 2.94 | 6 | 16.30 | 4.37 | 5 | 17.00 | 3.00 |
| Calcium, total (mg/dL) | 60 | 6 | 11.00 | 0.96 | 6 | 10.30 | 0.41 | 6 | 9.90 | 0.46 |
|  | 420 | 6 | 14.60 | 1.92 | 6 | 13.60 | 1.60 | 5 | 12.30 | 0.42 |
| Chloride (mEq/L) | 60 | 6 | 94.70 | 2.73 | 6 | 94.70 | 2.50 | 6 | 92.20 | 0.75 |
|  | 420 | 6 | 97.50 | 5.24 | 6 | 96.70 | 2.80 | 5 | 94.00 | 1.87 |
| Cholesterol (mg/dL) | 60 | 6 | 80.30 | 19.49 | 6 | 91.20 | 17.81 | 6 | 100.50 | 11.33 |
|  | 420 | 6 | 71.80 | 11.69 | 6 | 73.20 | 19.75 | 5 | 75.20 | 8.32 |
| $CO_2$ (mEq/L) | 60 | 6 | 19.80 | 2.23 | 6 | 22.80 | 7.60 | 6 | 19.30 | 2.25 |
|  | 420 | 6 | 28.20 | 4.26 | 6 | 32.30 | 6.28 | 5 | 28.00 | 3.67 |
| CPK (mg/dL) | 60 | 5 | 3110.20 | 2214.32 | 6 | 1854.50 | 1855.35 | 6 | 2232.20 | 781.68 |
|  | 420 | 5 | 4239.40 | 2910.33 | 6 | 2232.70 | 2283.61 | 5 | 2345.00 | 246.61 |
| Creatinine (mg/dL) | 60 | 6 | 0.80 | 0.14 | 6 | 0.80 | 0.15 | 6 | 0.90 | 0.14 |
|  | 420 | 6 | 0.90 | 0.13 | 6 | 0.90 | 0.15 | 5 | 0.90 | 0.08 |
| GGT (units/L) | 60 | 6 | 30.80 | 11.00 | 6 | 38.30 | 5.57 | 6 | 30.70 | 4.72 |
|  | 420 | 6 | 30.80 | 13.96 | 6 | 28.80 | 16.89 | 5 | 32.00 | 4.06 |
| Globulin (mg/dL) | 60 | 6 | 1.40 | 0.25 | 6 | 1.30 | 0.43 | 6 | 1.50 | 0.23 |
|  | 420 | 6 | 1.20 | 0.20 | 6 | 1.00 | 0.29 | 5 | 1.30 | 0.22 |
| LDH (units/L) | 60 | 6 | 562.70 | 162.56 | 6 | 474.20 | 127.11 | 6 | 429.80 | 33.08 |
|  | 420 | 6 | 691.30 | 259.21 | 6 | 473.20 | 252.38 | 5 | 487.20 | 81.87 |
| Lipase (units/L) | 60 | 6 | 13.80 | 13.73 | 6 | 5.20 | 2.40 | 6 | 46.20 | 71.39 |
|  | 420 | 6 | 56.80 | 98.20 | 6 | 28.80 | 42.86 | 5 | 81.00 | 112.30 |
| Phosphorous (mg/dL) | 60 | 6 | 7.80 | 1.56 | 6 | 6.90 | 0.93 | 6 | 8.50 | 0.61 |
|  | 420 | 6 | 11.10 | 0.89 | 6 | 10.10 | 0.72 | 5 | 10.70 | 0.60 |
| Potassium (mEg/L) | 60 | 6 | 4.60 | 0.53 | 6 | 4.70 | 0.75 | 6 | 4.80 | 0.19 |
|  | 420 | 6 | 3.80 | 0.28 | 6 | 3.90 | 0.18 | 5 | 4.10 | 0.18 |
| SGOT (units/L) | 60 | 6 | 68.30 | 31.49 | 6 | 55.70 | 32.13 | 6 | 51.70 | 8.80 |
|  | 420 | 6 | 86.20 | 35.50 | 6 | 60.70 | 31.68 | 5 | 61.60 | 5.98 |
| SGPT (units/L) | 60 | 6 | 28.20 | 9.20 | 6 | 26.70 | 8.78 | 6 | 30.70 | 5.61 |
|  | 420 | 6 | 27.70 | 6.22 | 6 | 23.30 | 7.71 | 5 | 26.00 | 4.30 |
| Sodium (mEg/L) | 60 | 6 | 136.70 | 2.16 | 6 | 137.50 | 2.43 | 6 | 134.30 | 2.34 |
|  | 420 | 6 | 146.30 | 4.13 | 6 | 148.50 | 4.18 | 5 | 141.40 | 1.95 |
| Total Bilirubin (mg/dL) | 60 | 6 | 0.10 | 0.05 | 6 | 0.10 | 0.05 | 6 | 0.20 | 0.05 |
|  | 420 | 6 | 0.30 | 0.08 | 6 | 0.40 | 0.14 | 5 | 0.30 | 0.08 |
| Total Protein (gm/dL) | 60 | 6 | 4.70 | 0.66 | 6 | 4.70 | 0.31 | 6 | 4.70 | 0.27 |
|  | 420 | 6 | 4.60 | 0.45 | 6 | 4.30 | 0.40 | 5 | 4.70 | 0.27 |

TABLE 5

Juvenile Pig Summary Physiological Data Statistics Table

| Parameters | Time | N | Control Treated Mean | St Dev | N | Septic Treated Mean | St Dev | N | Septic Sham Mean | St Dev |
|---|---|---|---|---|---|---|---|---|---|---|
| Mean Arterial Pressure | 60 | 6 | 74.20 | 14.26 | 6 | 86.30 | 5.72 | 6 | 84.70 | 15.12 |
| (mmHg) | 420 | 6 | 88.70 | 8.26 | 6 | 87.30 | 15.21 | 5 | 86.60 | 13.30 |
| Mean Cardiac Output | 60 | 3 | 2.10 | 0.68 | 6 | 1.60 | 0.38 | 6 | 2.20 | 0.38 |
| (mmHg) | 420 | 3 | 2.40 | 0.53 | 6 | 2.00 | 0.54 | 5 | 2.40 | 0.28 |
| Pulmonary Artery Pressure | 60 | 3 | 6.30 | 1.53 | 6 | 5.30 | 1.63 | 6 | 7.00 | 2.76 |
| (mmHg) | 420 | 3 | 7.30 | 1.15 | 6 | 5.50 | 2.07 | 5 | 6.80 | 4.76 |
| pH | 60 | 6 | 7.42 | 0.04 | 6 | 7.40 | 0.03 | 6 | 7.44 | 0.09 |
|  | 420 | 6 | 7.47 | 0.02 | 6 | 7.46 | 0.01 | 5 | 7.48 | 0.02 |
| Pulse (beats/min) | 60 | 6 | 135.80 | 18.00 | 6 | 130.00 | 10.95 | 6 | 156.70 | 21.60 |
|  | 420 | 6 | 138.30 | 17.80 | 6 | 141.70 | 17.22 | 5 | 152.00 | 17.89 |
| Respiration | 60 | 6 | 46.30 | 16.02 | 6 | 21.00 | 8.37 | 6 | 36.70 | 13.72 |
| (breaths/min) | 420 | 6 | 55.00 | 18.36 | 6 | 40.00 | 8.20 | 5 | 85.60 | 21.51 |
| Temperature (°C.) | 60 | 6 | 39.50 | 0.87 | 6 | 39.80 | 0.80 | 6 | 41.00 | 0.50 |
|  | 40 | 6 | 38.70 | 1.05 | 4 | 38.70 | 0.31 | 5 | 39.20 | 0.59 |
| pCO2 (mmHg) | 60 | 6 | 29.50 | 1.61 | 6 | 33.60 | 2.48 | 6 | 24.90 | 2.89 |
|  | 420 | 5 | 36.90 | 1.49 | 6 | 36.10 | 1.09 | 5 | 33.10 | 2.88 |
| pO2 (mmHg) | 60 | 6 | 83.30 | 12.51 | 6 | 70.40 | 4.96 | 6 | 71.80 | 11.91 |
|  | 420 | 5 | 82.30 | 5.92 | 6 | 75.90 | 4.03 | 5 | 67.70 | 4.85 |

TABLE 6

Healthy Young Pig Summary Hematology Statistics Table

| Parameters | Time | N | Test Mean | St Dev | N | Sham Mean | St Dev |
|---|---|---|---|---|---|---|---|
| Fibrinogen (mg/dL) | 0 | 6 | 389.70 | 102.55 | 6 | 457.80 | 46.55 |
|  | 300 | 4 | 298.00 | 110.60 | 4 | 371.30 | 34.18 |
| Hemoglobin (%) | 0 | 6 | 11.20 | 1.82 | 4 | 10.60 | 0.90 |
|  | 300 | 4 | 8.40 | 0.45 | 6 | 7.70 | 0.72 |
| Platelets (cells/cu. mm.) | 0 | 6 | 851833.30 | 550422.20 | 4 | 919000.00 | 175988.60 |
|  | 300 | 4 | 593333.30 | 337073.7 | 6 | 741250.00 | 168960.30 |
| Red Blood Cells (cells/cu. mm.) | 0 | 6 | 6375000.00 | 1010836.00 | 4 | 6147500.00 | 438584.70 |
|  | 300 | 4 | 4780000.00 | 279213.20 | 6 | 4492500.00 | 475491.00 |
| White Blood Cells (cells/cu. mm.) | 0 | 6 | 22883.30 | 7855.30 | 4 | 19600.00 | 8785.21 |
|  | 300 | 4 | 17350.00 | 5102.45 | 6 | 15125.00 | 6853.89 |

TABLE 7

Healthy Young Pig Summary Chemistry Statistics Table

| Parameters | Time | N | Test Mean | St Dev | N | Sham Mean | St Dev |
|---|---|---|---|---|---|---|---|
| Albumin (gm/L) | 0 | 6 | 3.10 | 0.55 | 6 | 2.80 | 0.46 |
|  | 300 | 6 | 2.80 | 0.35 | 6 | 2.60 | 0.29 |
| Alkaline Phosphatase (units/L) | 0 | 6 | 120.70 | 22.97 | 6 | 112.30 | 31.85 |
|  | 300 | 6 | 93.70 | 15.21 | 6 | 85.70 | 27.25 |
| BUN (mg/dL) | 0 | 6 | 10.20 | 1.47 | 6 | 11.70 | 2.42 |
|  | 300 | 6 | 11.70 | 2.94 | 6 | 12.30 | 3.78 |
| Calcium (mg/dL) | 0 | 6 | 10.00 | 0.49 | 6 | 9.80 | 0.50 |
|  | 300 | 6 | 15.50 | 2.17 | 6 | 14.40 | 1.43 |
| Chloride (mEq/L) | 0 | 6 | 106.50 | 4.97 | 6 | 106.50 | 7.32 |
|  | 300 | 6 | 106.70 | 3.01 | 6 | 106.80 | 5.00 |
| Cholesterol (mg/dL) | 0 | 6 | 88.20 | 18.29 | 6 | 95.30 | 28.10 |
|  | 300 | 6 | 59.50 | 12.42 | 6 | 63.50 | 18.05 |
| CO2 (mEq/L) | 0 | 6 | 22.70 | 3.01 | 6 | 25.20 | 3.49 |
|  | 300 | 6 | 25.30 | 2.94 | 6 | 31.20 | 5.71 |
| Creatinine (mg/dL) | 0 | 6 | 1.60 | 0.30 | 6 | 1.50 | 0.27 |
|  | 300 | 6 | 1.60 | 0.26 | 6 | 1.40 | 0.27 |
| Globulin (mg/dL) | 0 | 6 | 2.90 | 0.58 | 6 | 3.00 | 0.52 |
|  | 300 | 6 | 2.10 | 0.48 | 6 | 2.30 | 0.24 |
| Glucose (mg/dL) | 0 | 6 | 87.80 | 57.73 | 6 | 126.50 | 38.66 |
|  | 300 | 6 | 204.20 | 78.92 | 6 | 179.70 | 57.56 |
| Phosphorous (mg/dL) | 0 | 6 | 9.20 | 0.93 | 6 | 7.50 | 0.63 |
|  | 300 | 6 | 10.80 | 0.83 | 6 | 10.60 | 0.85 |
| Potassium (mEq/L) | 0 | 6 | 4.20 | 0.67 | 6 | 3.80 | 0.28 |
|  | 300 | 6 | 3.80 | 0.61 | 6 | 3.40 | 0.39 |
| SGOT (units/L) | 0 | 6 | 31.30 | 9.73 | 6 | 28.70 | 9.24 |
|  | 300 | 6 | 41.20 | 16.19 | 6 | 31.30 | 9.40 |
| SGPT (units/L) | 0 | 6 | 25.30 | 4.46 | 6 | 21.30 | 4.37 |
|  | 300 | 6 | 21.30 | 3.56 | 6 | 34.80 | 37.39 |
| Sodium (mEq/L) | 0 | 6 | 143.50 | 1.87 | 6 | 144.20 | 5.31 |
|  | 300 | 6 | 145.80 | 2.64 | 6 | 148.00 | 5.06 |
| Total Bilirubin (mg/dL) | 0 | 6 | 0.10 | 0.05 | 6 | 0.20 | 0.08 |
|  | 300 | 6 | 0.30 | 0.23 | 6 | 0.20 | 0.08 |
| Total Protein (gm/dL) | 0 | 6 | 6.00 | 0.47 | 6 | 5.90 | 0.52 |
|  | 300 | 6 | 4.90 | 0.26 | 6 | 4.90 | 0.31 |

TABLE 8

Healthy Young Pig Summary Physiological Data Statistics Table

| Parameters | Time | N | Test Mean | St Dev | N | Sham Mean | St Dev |
|---|---|---|---|---|---|---|---|
| Base Excess (mmol/L) | 0 | 6 | 0.60 | 3.07 | 6 | -0.40 | 1.97 |
|  | 300 | 6 | 2.70 | 2.33 | 6 | 3.10 | 1.55 |
| Compliance | 0 | 6 | 29.20 | 1.33 | 6 | 30.80 | 1.47 |
|  | 300 | 6 | 29.20 | 1.33 | 6 | 32.30 | 1.86 |
| Central Venous Pressure (mmHg) | 0 | 6 | 2.00 | 2.45 | 6 | 2.20 | 2.56 |
|  | 300 | 6 | 4.00 | 2.10 | 6 | 4.00 | 2.83 |
| Bicarbonate (mmol/L) | 0 | 6 | 25.00 | 1.79 | 6 | 24.30 | 1.63 |
|  | 300 | 6 | 26.30 | 2.88 | 6 | 26.80 | 1.72 |
| Ionized Calcium (mg/dL) | 0 | 6 | 1.40 | 0.14 | 6 | 1.40 | 0.08 |
|  | 300 | 6 | 0.80 | 0.08 | 6 | 0.80 | 0.14 |
| Mean Arterial Pressure | 0 | 6 | 59.00 | 4.05 | 6 | 63.00 | 5.33 |
|  | 300 | 6 | 52.80 | 7.19 | 6 | 57.20 | 6.37 |
| Mean Cardiac Output (mmHg) | 0 | 6 | 4.50 | 1.55 | 6 | 5.20 | 1.00 |
|  | 300 | 6 | 3.80 | 0.53 | 6 | 4.60 | 0.49 |
| Pulmonary Artery Pressure (mmHg) | 0 | 6 | 11.00 | 2.61 | 6 | 13.00 | 2.61 |
|  | 300 | 6 | 13.30 | 1.86 | 6 | 13.50 | 3.15 |
| PCO2 (mmHg) | 0 | 6 | 41.70 | 4.01 | 6 | 41.00 | 3.74 |
|  | 300 | 6 | 38.50 | 6.72 | 6 | 38.40 | 3.14 |
| pH | 0 | 6 | 7.40 | 0.07 | 6 | 7.40 | 0.04 |
|  | 300 | 6 | 7.40 | 0.04 | 6 | 7.40 | 0.03 |
| PO2 (mmHg) | 0 | 6 | 488.80 | 38.43 | 6 | 418.70 | 75.49 |
|  | 300 | 6 | 486.50 | 26.10 | 6 | 441.70 | 65.29 |
| Peak Pressure (mmHg) | 0 | 6 | 19.00 | 1.67 | 6 | 19.00 | 0.89 |
|  | 300 | 6 | 19.00 | 1.67 | 6 | 18.20 | 1.47 |
| Pulse (beats/min) | 0 | 6 | 140.70 | 31.67 | 6 | 158.20 | 29.84 |
|  | 300 | 6 | 112.70 | 11.86 | 6 | 127.00 | 16.35 |
| Wedge (mmHg) | 0 | 6 | 4.00 | 3.22 | 6 | 3.80 | 2.23 |
|  | 300 | 6 | 5.80 | 1.94 | 6 | 5.00 | 2.61 |
| Respiration (breaths/min) | 0 | 6 | 9.80 | 1.60 | 6 | 11.50 | 1.22 |
|  | 300 | 6 | 10.00 | 2.19 | 6 | 12.00 | 1.10 |
| Temperature (°C.) | 0 | 6 | 37.10 | 0.82 | 6 | 37.10 | 1.23 |
|  | 300 | 6 | 35.80 | 1.20 | 6 | 36.00 | 1.55 |
| TV | 0 | 6 | 550.00 | 54.77 | 6 | 583.30 | 25.82 |
|  | 300 | 6 | 550.00 | 54.77 | 6 | 583.30 | 25.82 |

We claim as our invention:

1. A method for removing selected factors in a mammalian subject's blood or blood component, comprising contacting the blood or blood component with a composition of matter comprising pretreated amorphous, particulate, granular silica and silica pretreating agent selected from the group consisting of heparin and albumin, wherein the silica has a specific surface area of at least 150 m$^2$/g, and contains between 0.5 cc/g and 2.5 cc/g of porosity, whereby at least a portion of the selected factors are removed from the blood or blood component.

2. The method of claim 1, wherein the specific surface area of the silica is between 150 µm$^2$/g and 1000 m$^2$/g.

3. The method of claim 2, wherein the specific surface area of the silica is between 200 µm$^2$/g and 600 m$^2$/g.

4. The method of claim 1 wherein the porosity of the silica is between 0.8 cc/g and 1.5 cc/g.

5. The method of claim 1 wherein the silica is substantially chemically unmodified.

6. The method of claim 1 in which the silica particles have a mean diameter less than about 1 mm.

7. The method of claim 6 in which the silica particles have a mean diameter between about 50 and 250 microns.

8. The method of claim 1 in which the silica has a mean pore diameter of about 30 Å to 300 Å.

9. The method of claim 8 in which the silica has a mean pore diameter of about 60 Å to 200 Å.

10. The method of claim 1 comprising albumin in an amount between 1% and 25% by weight of the silica pretreating agent.

11. The method of claim 10 comprising albumin in an amount between 2.5% and 5% of the silica pretreating agent.

12. The method of claim 1 in which the silica pretreating agent is substantially devoid of covalent attachment to the silica.

13. The method of claim 1 in which the selected factors comprise cytokines, complement molecules, serotonin, histamine, cholesterol molecules, a myoglobin component, angiogenesis factor or a pharmaceutical.

14. The method of claim 1 further comprising a step of subjecting the subject's blood to an anticoagulation regimen.

15. The method of claim 14 wherein the anticoagulation regimen comprises use of citrate.

16. The method of claim 14 wherein the anticoagulation regimen comprises use of citrate and heparin.

17. A method for treating a condition characterized by the presence of selected factors in a mammalian subject's blood or blood component, comprising contacting the blood or blood component with a composition of matter comprising pretreated amorphous, particulate, granular silica and silica pretreating agent selected from the group consisting of heparin and albumin, wherein the silica has a specific surface area of at least 150 $m^2/g$, contains between 0.5 cc/g and 2.5 cc/g of porosity and introducing the contacted blood or blood component to the subject.

18. The method of claim 17 wherein the condition is septic shock syndrome.

19. The method of claim 17 wherein the condition is capillary leak syndrome.

20. The method of claim 17 wherein the condition is acute renal failure.

21. The method of claim 17 wherein the condition is pharmaceutical overdose.

22. The method of claim 17 wherein the selected factors comprise serotonin, histamine, complement molecules, cytokines, interferon, tumor necrosis factor (TNF), cholesterol molecules, anglogenesis factor, a myoglobin component, or a pharmaceutical.

23. A composition of matter capable of removing selected factors from blood or a blood component, composition of matter comprising pretreatment amorphous, particulate, granular silica and silica pretreating agent, wherein the silica has a specific surface area of at least 150 $m^2/g$, and contains between 0.5 cc/g and 2.5 cc/g of porosity, and wherein the silica pretreating agent is heparin or albumin.

24. The composition of claim 23 wherein the specific surface area of the silica is between 150 $\mu m^2/g$ and 1000 $m^2/g$.

25. The composition of claim 24, wherein the specific surface area of the silica is between 200 $m^2/g$ and 600 $m^2/g$.

26. The composition of claim 23 wherein the porosity of the silica is between 0.8 cc/g and 1.5 cc/g.

27. The composition of claim 23 wherein the silica is substantially unmodified chemically.

28. The composition of claim 23 in which the silica particles have a mean diameter less than about 1 mm.

29. The composition of claim 28 in which the silica particles have a mean diameter between about 50 and 250 microns.

30. The composition of claim 23 in which the silica has a mean pore diameter of about 30 Å to 300 Å.

31. The composition of claim 30 in which the silica has a mean pore diameter of about 60 Å to 200 Å.

32. The composition of claim 23 comprising albumin in an amount between 1% and 25% by weight of the silica pretreating agent.

33. The composition of claim 32 comprising albumin in an amount between 2.5% and 5% by weight of the silica pretreating agent.

34. The composition of claim 23 in which the silica pretreating agent is substantially devoid of covalent attachment to the silica.

35. The composition of claim 23 in which the selected factors comprise cytokines, complement molecules, serotonin, histamine, cholesterol molecules, or angiogenesis factor.

36. The composition of claim 23, wherein the composition is immobilized within a porous solid matrix.

37. A medical device containing the composition of claim 23.

38. A composition of matter according to claim 23, wherein the silica is substantially unmodified chemically.

39. The method of claim 1, wherein said blood component is plasma.

40. The method of claim 17, wherein said blood component is plasma.

41. A composition of matter according to claim 23, wherein the blood component is plasma.

42. A composition of matter according to claim 38, wherein the blood component is plasma.

* * * * *